(12) United States Patent
Cost et al.

(10) Patent No.: US 9,005,973 B2
(45) Date of Patent: Apr. 14, 2015

(54) TARGETED GENOMIC MODIFICATION WITH PARTIALLY SINGLE-STRANDED DONOR MOLECULES

(75) Inventors: Gregory J. Cost, Berkeley, CA (US); Dmitry M. Guschin, Albany, CA (US); Fyodor Urnov, Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 0 days.

(21) Appl. No.: 13/135,558

(22) Filed: Jul. 8, 2011

(65) Prior Publication Data

US 2011/0287545 A1 Nov. 24, 2011

Related U.S. Application Data

(63) Continuation of application No. 12/931,760, filed on Feb. 9, 2010.

(60) Provisional application No. 61/337,756, filed on Feb. 9, 2010, provisional application No. 61/342,934, filed on Apr. 21, 2010.

(51) Int. Cl.
| | | |
|---|---|---|
| *C12P 21/06* | (2006.01) | |
| *C12N 15/00* | (2006.01) | |
| *C12N 15/87* | (2006.01) | |
| *C12N 9/22* | (2006.01) | |
| *C12N 15/90* | (2006.01) | |

(52) U.S. Cl.
CPC ................ *C12N 9/22* (2013.01); *C12N 15/907* (2013.01); *C07K 2319/81* (2013.01); *C07K 2319/80* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,528,313 B1 | 3/2003 | Le Mouellic et al. | |
| 6,528,314 B1 | 3/2003 | Le Mouellic et al. | |
| 6,534,261 B1 | 3/2003 | Cox et al. | |
| 6,599,692 B1 | 7/2003 | Case et al. | |
| 6,607,882 B1 | 8/2003 | Cox et al. | |
| 6,689,558 B2 | 2/2004 | Case | |
| 6,824,978 B1 | 11/2004 | Cox et al. | |
| 6,903,185 B2 | 6/2005 | Kim et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,153,949 B2 | 12/2006 | Kim et al. | |
| 7,163,824 B2 | 1/2007 | Cox et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2006/0063231 A1 | 3/2006 | Li et al. | |
| 2006/0188987 A1 | 8/2006 | Guschin et al. | |
| 2007/0218528 A1 | 9/2007 | Miller et al. | |
| 2008/0131962 A1 | 6/2008 | Miller | |
| 2008/0159996 A1 | 7/2008 | Ando et al. | |
| 2008/0299580 A1 | 12/2008 | DeKelver et al. | |
| 2009/0117617 A1 | 5/2009 | Holmes et al. | |
| 2009/0263900 A1 | 10/2009 | DeKelver et al. | |
| 2009/0275087 A1 | 11/2009 | Mikawa | |
| 2009/0305346 A1 | 12/2009 | Miller | |
| 2009/0305419 A1 | 12/2009 | Miller | |
| 2010/0129869 A1 | 5/2010 | Liu et al. | |
| 2011/0145940 A1* | 6/2011 | Voytas et al. | ................... 800/13 |

FOREIGN PATENT DOCUMENTS

| | | |
|---|---|---|
| GB | 2338237 A | 12/1999 |
| WO | 95/19431 A1 | 7/1995 |
| WO | WO 95/19431 A1 | 7/1995 |
| WO | 96/06166 A1 | 2/1996 |
| WO | WO 96/06166 A1 | 2/1996 |
| WO | 98/37186 A1 | 8/1998 |

(Continued)

OTHER PUBLICATIONS

Tsuchiya et al., Improved Gene Correction Efficiency with a Tailed Duplex DNA Fragment; Biochemistry, vol. 47, pp. 8754-8759, 2008.*

Daley and Wilson, Rejoining of DNA Double-Strand Breaks as a Function of Overhang Length; Mol Cell Bio, vol. 25, No. 3, pp. 896-906, 2005.*

Radecke et al., Physical incorporation of a single-stranded oligodeoxynucleotide during targeted repair of a human chromosomal locus; The Journal of Gene Medicine, vol. 8, pp. 217-228, 2006.*

Wah et al., Structure of FokI has implications for DNA cleavage; PNAS, vol. 95, pp. 10564-10569, 1998.*

Schiestl et al., Integration of DNA fragments by illegitimate recombination in *Saccharomyces cerevisiae*; PNAS, vol. 88, pp. 7585-7589, 1991.*

(Continued)

*Primary Examiner* — Jennifer Dunston
*Assistant Examiner* — Addison D Ault
(74) *Attorney, Agent, or Firm* — Pasternak Patent Law; Susan Abrahamson

(57) ABSTRACT

Disclosed herein are donor molecules comprising single-stranded complementary regions flanking one or more sequences of interest. The donor molecules and/or compositions comprising these molecules can be used in methods for targeted integration of an exogenous sequence into a specified region of interest in the genome of a cell.

7 Claims, 10 Drawing Sheets

(56) References Cited

FOREIGN PATENT DOCUMENTS

| WO | WO 98/37186 A1 | 8/1998 |
|---|---|---|
| WO | 98/53057 A1 | 11/1998 |
| WO | 98/53058 A1 | 11/1998 |
| WO | 98/53059 A1 | 11/1998 |
| WO | 98/53060 A1 | 11/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | 98/54311 A1 | 12/1998 |
| WO | WO 98/54311 A1 | 12/1998 |
| WO | 00/27878 A1 | 5/2000 |
| WO | WO 00/27878 A1 | 5/2000 |
| WO | 01/53480 A1 | 7/2001 |
| WO | WO 01/53480 A1 | 7/2001 |
| WO | 01/60970 A2 | 8/2001 |
| WO | WO 01/60970 A2 | 8/2001 |
| WO | 01/88197 A2 | 11/2001 |
| WO | WO 01/88197 A2 | 11/2001 |
| WO | 02/16536 A1 | 2/2002 |
| WO | WO 02/16536 A1 | 2/2002 |
| WO | 02/057293 A2 | 7/2002 |
| WO | WO 02/057293 A2 | 7/2002 |
| WO | 02/077227 A2 | 10/2002 |
| WO | WO 02/077227 A2 | 10/2002 |
| WO | 02/099084 A2 | 12/2002 |
| WO | WO 02/099084 A2 | 12/2002 |
| WO | 03/016496 A2 | 2/2003 |
| WO | WO 03/016496 A2 | 2/2003 |
| WO | 2007/014275 A2 | 1/2007 |
| WO | WO 2007/014275 A2 | 1/2007 |
| WO | 2008/133938 A2 | 11/2008 |
| WO | WO 2008/133938 A2 | 11/2008 |
| WO | WO 2009/131632 A1 | 10/2009 |
| WO | WO 2010/079430 A1 | 7/2010 |
| WO | WO 2010/113031 A2 | 10/2010 |
| WO | WO 2010/143917 A2 | 12/2010 |
| WO | WO 2011/146121 A1 | 11/2011 |

OTHER PUBLICATIONS

Rouet et al., Introduction of double-strand breaks into the genome of mouse cells by expression of a rare-cutting endonuclease; Mol. Cell. Biol. vol. 14, No. 12, pp. 8096-8106, 1994.*
Roth et al., Nonhomologous Recombination in Mammalian Cells: Role for Short Sequence Homologies in the Joining Reaction; Mol. Cell. Biol. vol. 6, No. 12, pp. 4295-4304, 1984.*
Lin et al., Nonhomologous Recombination in Mammalian Cells: Role for Short Sequence Homologies in the Joining Reaction; NAR, vol. 29, No. 18, pp. 3975-3981, 2001.*
Beumer et al., "Comparing ZFNs and TALENs for Gene Targeting in Drosophila," *Genetics* doi:10.1534/g3.113.007.007260 (2013).
Boch et al., "Breaking the Code of DNA Binding Specificty of TAL-Type III Effectors," *Science* 326(5959):1509-1512 (2009).
Boch et al., "Tales of Genome Targeting," *Nature Biotechnology* 29(2):135-136 (2011).
Cai et al., "Targeted Transgene Integration in Plant Cells Using Designed Zinc Finger Nucleases," *Plant Molecular Biology* 69(6):699-709 (2008).
Christian et al., "Targeting DNA Double-Strand Breaks With TAL Effector Nucleases," *Genetics* 186(2):757-761 (2010).
Cristea et al., "In Vivo Cleavage of Transgene Donors Promotes Nuclease-Mediated Targeted Integration," *Genome Research* 23(3):539-546 (2012).
Kim et al., "TALENs and ZFNs Are Associated With Different Mutation Signatures," *Nature Methods* 10(3):185 (2013).
Li et al., "TAL Nucleases (TALNs):Hybrid Proteins Composed of TAL Effectors and FOKI DNA-Cleavage Domain," *Nucleic Acids Research* 39(1):359-372 (2011).
Maresca et al., "Obligate Ligation-Gated Recombination (OBLIGARE):Custom-Designed Nuclease-Mediated Targeted Integration Through Nonhomologous End Joining," *Genome Research* 23(3):539-546 (2012).
Moscou et al., "A Simple Cipher Governs DNA Recognition by TAL Effectors," *Science* 326(5959):1501 (2009).
Piganeau et al., "Cancer Translocations in Human Cells Induced by Zinc Finger and Tale Nucleases Supplementary Information," *Genome Research* 23(7):1182-1193 (2013).
Zeevi et al., "Increasing Cloning Possibilities Using Artificial Zinc Finger Nucleases," *Proceedings of the National Academy of Sciences of the United States of America* 105(35):12785-12790 (2008).
Beerli, et al., "Engineering Polydactyl Zinc-Finger Transcription Factors," *Nature Biotechnology* 20:135-141 (2002).
Bitinate, et al., "FOKI Dimerization Is Required for DNA Cleavage," *PNAS USA* 95:10570-10575 (1998).
Capecchi, et al., "Altering the Genome by Homologous Recombination," *Science* 244:1288-1292 (1989).
Choo, et al., "Advances in Zinc Finger Engineering," *Curr. Opin. Struct. Biol.* 10:411-416 (2000).
Ciafri, et al., "Stability and Functional Effectiveness of Phosphorothioate Modified Duplex Dna and Synthetic 'Mini-Genes'," *Nucleic Acids Res* 23(20):4134-4142 (1995).
DeKelver, et al., "Functional Genomics, Proteomics, and Regulatory DNA Analysis in Isogenic Settings Using Zinc Finger Nuclease-Driven Trans Genesis Into a Safe Harbor Locus in the Human Genome," *Genome Res* 20:1133-1142 (2010).
D'Halluin, et al., "Homologous Recombination: A Basis for Targeted Genome Optimization in Crop Species Such As Maize," *Plant Biotechnology J.* 6:93-102 (2008).
Haviv-Chesnner, et al., "Capture of Linear Fragments At a Double-Strand Break in Yeast," *Nucleic Acids Res* 35:5192-5202 (2007).
Hockemeyer, et al., "Efficient Targeting of Expressed and Silent Genes in Human ESCS and IPSCS Using Zinc-Finger Nucleases," *Nat Biotechnol* 27:851-857 (2009).
Isalan et al., "A Rapid, Generally Applicable Method to Engineer Zinc Fingers Illustrated by Targeting the HIV-1 Promoter," *Nat Biotechnol* 19:656-660 (2001).
Ishibashi, et al., "Nonhomologous Chromosomal Integration of Foreign DNA Is Completely Dependent on MUS-53 (Human LIG4 Homolog) in Neurospora," *Proc Nat'l Acad Sci USA* 103(40):14871-14876 (2006).
Johansson, et al., "PCR-Generated Linear DNA Fragments Utilized As a Hantavirus DNA Vaccine," *Vaccine* 20(27-28):3379-3388 (2002).
Kim, et al., "Chimeric Restriction Endonuclease," *PNAS USA* 91:883-887 (1994).
Kim, et al., "Insertion and Deletion Mutants of FOKI Restriction Endonuclease," *J. Biol. Chem.* 269:31978-31982 (1994).
Koller, et al., "Germ-Line Transmission of a Planned Alteration Made in a Hypdxanthine Phosphoribosyltransferase Gene by Homologous Recombination in Embryonic Stem Cells," *Proc Nat'l Acad Sci USA* 86:8927-8931 (1989).
Lee, et al., "Targeted Chromosomal Deletions in Human Cells Using Zinc Finger Nucleases," *Genome Res* 20(1):81-89 (2010).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Lin, et al., "Promiscuous Patching of Broken Chromosomes in Mammalian Cells With Extrachromosomal DNA," *Nucleic Acids Res* 29:3975-3981 (2001).
Lin, et al., "Capture of DNA Sequences At Double-Strand Breaks in Mammalian Chromosomes," *Genetics* 158:1665-1674 (2001).
Lisby, M., et al., "DNA Damage Checkpoint and Repair Centers," *Curr Opin Cell Biol* 16:328-334 (2004).
Liu, P.Q., et al., "Generation of a Triple-Gene Knockout Mammalian Cell Line Using Engineered Zinc-Finger Nucleases," *Biotechnol Bioeng* 106:97-105 (2010).
Lombardo, et al., "Gene Editing in Human Stem Cells Using Zinc Finger Nucleases and Integrase-Defective Lentiviral Vector Delivery," *Nature Biotechnology* 25:1298-1306 (2007).
Miller, et al., "Repetitive Zinc-Binding Domains in the Protein Transcription Factor IIIA From Xenopus Oocytes," *EMBO J.* 4:1609-1614 (1985).

(56) References Cited

OTHER PUBLICATIONS

Miller, et al., "A Tale Nuclease Architecture for Efficient Genome Editing," *Nature Biotechnology* 29:143-148 (2011).
Moehle, et al., "Targeted Gene Addition Into a Specified Location in the Human Genome Using Designed Zinc Finger Nucleases," *PNAS* 104:3055-3060 (2007).
Moore, et al., "Capture of Retrotransposon DNA at the Sites of Chromosomal Double-Strand Breaks," *Nature* 383:644-646 (1996).
Moore, et al., "Design of Polyzinc Finger Peptides With Structured Linkers," *PNAS USA* 98:1432-1436 (2001).
Moore, et al., "Improved DNA Binding Specificity From Polyzinc Finger Peptides by Using Strings of Two-Finger Units," *PNAS USA* 98:1437-1441 (2001).
Orlando, et al., "Zinc-Finger Nuclease-Driven Targeted Integration Into Mammalian Genomes Using Donors With Limited Chromosomal Homology," *Nucleic Acids Research* 38:e152 (2010).
Pabo, et al., "Design and Selection of Novel CYS2-HIS2 Zinc Finger Proteins," *Ann. Rev. Biochem.* 70:313-340 (2001).
Perez, et al., "Establishment of HIV-1 Resistance in CD4+ T Cells by Genome Editing Using Zinc-Finger Nucleases," *Nature Biotechnology* 26:808-816 (2008).
Rhodes, et al., "Zinc Fingers: They Play a Key Part in Regulating the Activity of Genes in Many Species, From Yeast to Humans. Fewer Than 10 Years Ago No On Knew They Existed." *Scientific American* 268:56-65 (1993).
Rouet, et al., "Expression of a Site-Specific Endonuclease Stimulates Homologous Recombination in Mammalian Cells," *Proc Nat'l Acad Sci USA* 91:6064-6068 (1994).
Sambrook, et al., "Cloning in Plasmid Vectors," Molecular Cloning: A Laboratory Manual, 3$^{rd}$ Edition, Cold Spring Harbor Press, pp. 1.19-1.22 (2001).
Segal, et al., "Custom DNA-Binding Proteins Come of Age: Polydactyl Zinc-Finger Proteins," *Curr. Opin. Biotechnol.* 12:632-637 (2001).
Smith, et al., "Requirements for Double-Strand Cleavage by Chimeric Restriction Enzymes With Zinc Finger DNA-Recognition Domains," *Nucleic Acids Research* 28:3361-3369 (2000).
Storici, et al., "Chromosomal Site-Specific Double-Strand Breaks Are Efficiently Targeted for Repair by Oligonucleotides in Yeast," *Proc Nat'l Acad Sci USA* 100:14994-14999 (2003).
Storici, et al., "Conservative Repair of a Chromosomal Double-Strand Break by Single-Strand DNA Through Two Steps of Annealing," *Mol Cell Biol* 26:7645-7657 (2006).
Terada, et al., "Efficient Gene Targeting by Homologous Recombination in Rice," *Nat Biotechnology* 20:1030-1034 (2002).
Terada, et al., "Gene Targeting by Homologous Recombination as a Biotechnological Tool for Rice Functional Genomics," *Plant Physiol* 144:846-856 (2007).
Thomas, et al., "High Frequency Targeting of Genes to Specific Sites in the Mammalian Genome," *Cell* 44:419-428 (1986).
Umov, et al., "Highly Efficient Endogenous Human Gene Correction Using Designed Zinc-Finger Nucleases," *Nature* 435:646-651 (2005).
Urnov, F.D., et al., "Genome Editing With Engineered Zinc Finger Nucleases," *Nat Rev Genet* 11:636- 646 (2010).
Weterings, et al., "The Mechanism of Non-Homologous End-Joining: A Synopsis of Synapsis," *DNA Repair (Amst)* 3:1425-1435 (2004).
Yu, et al., "Patching Broken Chromosomes With Extranuclear Cellular DNA," *Mol Cell* 4:873-881 (1999).

* cited by examiner

GCGGAGCCATCTGGCCGGGTTGG|CTGG|TTATAACCGCGCAGATTCTGTTCAC
CGCCTCGGTAGACCGGCCCAACCGACC|AATATTGGCGCGTCTAAGACAAGTG

CTGGGTACGGATCCAAGCTTCGTCGACCTAGCC
CATGCCTAGGTTCGAAGCAGCTGGATCGGGACC

B

GCGGAGCCATCTGGCCGGGTTGGC|TGGT|TATAACCGCGCAGATTCTGTTCAC
CGCCTCGGTAGACCGGCCCAACCGACCA|ATATTGGCGCGTCTAAGACAAGTG

TGGTGTACGGATCCAAGCTTCGTCGACCTAGCC
CATGCCTAGGTTCGAAGCAGCTGGATCGGACCA

C

|   | Oligo-derived Sequence | Genomic Sequence |   |
|---|---|---|---|
| expected | ATCCAAGCTTCGTCGACCTAGCC|CTGG|TATAACCGCGCAGATTCTGTT | | |
| | ATCCAAGCTTCGTCGACCTAGCCCTGGTTATAACCGCGCAGATTCTGTT | | x11 |
| | ATCCAAGCTTCGTCGACCTAGCC::::::::::GCGCAGATTCTGTT | | x1 |

D

|   | Oligo-derived Sequence | Genomic Sequence |   |
|---|---|---|---|
| expected | ATCCAAGCTTCGTCGACCTAGCC|TGG|TATAACCGCGCAGATTCTGTT | | |
| | ATCCAAGCTTCGTCGACCTAGCCTAGCCTAGCCTGGT::TAACCGCGCAGATTCTGTT | | x6 |
| | ATCCAAGCTTCGTCGACCTAGCCTAGCCTGG:TATAACCGCGCAGATTCTGTT | | x3 |
| | ATCCAAGCTTCGTCGACCTAGCCTGGT:GTA::::CGCGCAGATTCTGTT | | x2 |
| | ATCCAAGCTTCGTCGACCT:::::GGTTATAACCGCGCAGATTCTGTT | | x1 |

SEQUENCE LISTING

```
<160> NUMBER OF SEQ ID NOS: 113

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Asn Trp His Leu Gln Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp His Leu Thr Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

His Asn Tyr Ala Arg Asp Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Asn Ser Thr Arg Ile Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Ser Asn Leu Ala Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Thr Asp Tyr Leu Val Asp
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Asn Thr His Leu Thr Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gly Tyr Asn Leu Ala Gly
1               5

<210> SEQ ID NO 9
<211> LENGTH: 7
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ser Asp Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Asn Leu Arg Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Asp Thr Leu Ser Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Lys Asp Val Arg Ile Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp His Leu Ser Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Ser Asp Leu Arg Arg
```

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Asp His Leu Ser Gln
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Ala Asn Arg Thr Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp Asn Leu Ser Gln
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ser Asn Asp Arg Lys Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ser Ala Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 20

Arg Ser Asp Ala Leu Ala Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Asp Val Leu Ser Glu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Ser Gly His Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Arg Ser His Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Gly Asn Leu Ala Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Asp Ala Leu Ser Ala
1               5

<210> SEQ ID NO 26
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Arg Ser Asp Arg Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ser Asp His Leu Thr Asn
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Arg Ala Asn Leu Ser Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Asn Leu Ser Val
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Asn Ala Thr Arg Ile Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

```
Gln Ser Gly Ser Leu Thr Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Asp His Leu Ser Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Arg Ser Asn Arg Lys Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Ala Ala Leu Ser Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ser Ala Asp Arg Thr Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Ala Asn Leu Thr Arg
1               5

<210> SEQ ID NO 37
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 37

Arg Ser Asp Asn Leu Ala Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Asp Asn Leu Thr Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Asp His Leu Ser Glu
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Asn His His Arg Ile Asn
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Arg Gly Thr Leu Ala Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ser Gly His Leu Ala Arg
1               5

```
<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ser Asp Ala Leu Thr Gln
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp Asn Leu Thr Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Asp His Leu Ser Val
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Asp Asn Leu Ser Glu
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ser Lys Thr Arg Lys Asn
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

```
Thr Ser Ser Asp Arg Thr Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Arg Ser Asn Leu Val Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ser Asp Thr Leu Ser Val
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asn Ser Thr Arg Ile Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Asp Ala Leu Ser Val
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Ser Ser His Arg Thr Arg
1               5

<210> SEQ ID NO 54
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 54
ccccactgtg gggtggaggg gacagta                                             27

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
actagggaca ggattgtgtt cacagtca                                            28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gaatggtgca ggctgccata ccaactttt                                           28

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gttcccagga atgggcttgg ggtcaaag                                            28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aagctggtct ggtggctagg tagatcct                                            28

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gggctctgga aggcccactt cagggcct                                            28

<210> SEQ ID NO 60
<211> LENGTH: 28
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 60
atgtaacaaa ggactactct tccccag                                          28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atgagtcagt gaacagggaa tgggtgaa                                         28

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gccaggatta ggaggatggg atttggca                                         28

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cacgggccca gggtggggca gaaagccc                                         28

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aggattagga ggatgggatt tggcactg                                         28

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cagcacgggc ccagggtggg gcagaaag                                         28

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
atcaggaaga ggctgggtgt cacagcgt                                              28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcggccaggc caaggcagac tttctgac                                              28

<210> SEQ ID NO 68
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gccagcttag gtgagaattc ggcggatccc gaagcttgct aactcagcc                       49

<210> SEQ ID NO 69
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tggcggctga gttagcaagc ttcgggatcc gccgaattct cacctaagc                       49

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ccccttacct ctctagtctg tgc                                                   23

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ctcaggttct gggagagggt ag                                                    22

<210> SEQ ID NO 72
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctgggcttag gtgagaattc ggcggatccc gaagcttgct aactcagcc        49

<210> SEQ ID NO 73
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ccagggctga gttagcaagc ttcgggatcc gccgaattct cacctaagc        49

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gggtggcccg tttcatct                                          18

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgtgacaact ttcccatatc aca                                    23

<210> SEQ ID NO 76
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tttgggaatt cataacttcg tatagcatac attatacgaa gttatggatc c     51

<210> SEQ ID NO 77
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgcaggatcc ataacttcgt ataatgtatg ctatacgaag ttatgaattc       50

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gatagaacga gattccgtct tggtgg                                     26

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcagagcttt gatgtcctgg gact                                       24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
catctcacat ctggaccaca gccg                                       24

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgcgggcaa atagatcac                                             19

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Arg Ser Asn Arg Thr Thr
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Asn Ala His Arg Ile Asn
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 84

Arg Ser Asp Thr Leu Ser Glu
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Arg Ser Thr Arg Thr Asn
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Arg Ser Thr Arg Thr Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ser Asp Ser Leu Ser Lys
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Arg Ser Asn Leu Lys Val
1               5

<210> SEQ ID NO 89
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cactctgtgg aagt                                                       14

<210> SEQ ID NO 90
<211> LENGTH: 16
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 90
ttaaagcggc tccgaa                                                     16

<210> SEQ ID NO 91
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tgtcccctcc accccacagt ggggccacta gggacaggat tggtgacaga               50

<210> SEQ ID NO 92
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gaccccaagc ccattcctgg gaactggaat ggtgcaggct gccataccaa               50

<210> SEQ ID NO 93
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gtttcgtgtt cggagccgct taacccact ctgtggaagt gctcagcatt                50

<210> SEQ ID NO 94
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gcggagccat ctggccgggt tggctggtta taaccgcgca gattctgttc ac           52

<210> SEQ ID NO 95
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gtgaacagaa tctgcgcggt tataaccagc caacccggcc agatggctcc gc           52

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctgggtacgg atccaagctt cgtcgaccta gcc                               33

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ccagggctag gtcgacgaag cttggatccg tac                               33

<210> SEQ ID NO 98
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gcggagccat ctggccgggt tggctggtta taaccgcgca gattctgttc ac          52

<210> SEQ ID NO 99
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtgaacagaa tctgcgcggt tataaccagc caacccggcc agatggctcc gc          52

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tggtgtacgg atccaagctt cgtcgaccta gcc                               33

<210> SEQ ID NO 101
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
accaggctag gtcgacgaag ctttggatccg tac                              33

<210> SEQ ID NO 102
<211> LENGTH: 49
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 102
atccaagctt cgtcgaccta gccctggtta taaccgcgca gattctgtt                49

<210> SEQ ID NO 103
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
atccaagctt cgtcgaccta gccctggtta taaccgcgca gattctgtt                49

<210> SEQ ID NO 104
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atccaagctt cgtcgaccta gccgcgcaga ttctgtt                             37

<210> SEQ ID NO 105
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atccaagctt cgtcgaccta gcctggttat aaccgcgcag attctgtt                 48

<210> SEQ ID NO 106
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
atccaagctt cgtcgaccta gcctggttaa ccgcgcagat tctgtt                   46

<210> SEQ ID NO 107
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
atccaagctt cgtcgaccta gcctggtata accgcgcaga ttctgtt                  47

<210> SEQ ID NO 108
<211> LENGTH: 45
<212> TYPE: DNA
<213> ORGANISM: Artificial Sequence
<220> FEATURE:
<223> OTHER INFORMATION: Description of Artificial Sequence: Synthetic

```
<210> SEQ ID NO 109
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atccaagctt cgtcgaccta gcctggtgta cgcgcagatt ctgtt              45

<210> SEQ ID NO 109
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
atccaagctt cgtcgacctg gttataaccg cgcagattct gtt                43

<210> SEQ ID NO 110
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
atcaagctta tc                                                  12

<210> SEQ ID NO 111
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tttaacccac t                                                   11

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggaactggat gg                                                  12

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tggggccact ag                                                  12
```

TARGETED GENOMIC MODIFICATION WITH PARTIALLY SINGLE-STRANDED DONOR MOLECULES

CROSS-REFERENCE TO RELATED APPLICATIONS

This application is a continuation application of U.S. patent application Ser. No. 12/931,760, filed Feb. 9, 2011, which claims the benefit of U.S. Provisional Application Nos. 61/337,756, filed Feb. 9, 2010 and 61/342,934, filed Apr. 21, 2010, the disclosures of which are hereby incorporated by reference in their entireties.

TECHNICAL FIELD

The present disclosure is in the field of genome engineering, particularly targeted modification of the genome of a cell.

BACKGROUND

A major area of interest in genome biology, especially in light of the determination of the complete nucleotide sequences of a number of genomes, is targeted integration into genomic sequences. Attempts have been made to alter genomic sequences in cultured cells by taking advantage of the natural phenomenon of homologous recombination. See, for example, Capecchi (1989) Science 244:1288-1292; U.S. Pat. Nos. 6,528,313 and 6,528,314.

In addition, various methods and compositions for targeted cleavage of genomic DNA have been described. Such targeted cleavage events can be used, for example, to induce targeted mutagenesis, induce targeted deletions of cellular DNA sequences, and facilitate targeted recombination and targeted integration at a predetermined chromosomal locus. See, for example, United States Patent Publications 20030232410; 20050208489; 20050026157; 20050064474; and 20060188987, and International Publication WO 2007/014275, the disclosures of which are incorporated by reference in their entireties for all purposes. For example, targeted integration using zinc finger nucleases has been demonstrated with circular (plasmid) DNAs having long (~750 base pair) homology arms. See, Moehle et al. (2007)*Proc. Nat'l. Acad. Sci. USA* 104(9):3055-3060.

Targeted integration relies on manipulating normal cellular processes. Typically, cells often depend on homology-directed repair (HDR) which heals spontaneous double strand breaks (DSB) in the genome using the sister chromatid as a template. For targeted insertion of exogenous sequences of interest, the exogenous DNA sequence is constructed so that it is between the two regions in the donor plasmid that contain homology to the genomic location being targeted. The cellular DNA repair machinery will unwittingly copy this genetic information into the chromosome while healing any spontaneous DSB that may have occurred (See Thomas et al, (1986) *Cell* 44:419-428 and Koller et al, (1989) *Proc Natl Acad Sci USA* 86: 8927-8931).

In plants, biotechnology has emerged as an essential tool in efforts to meet the challenge of increasing global demand for food production. Conventional approaches to improving agricultural productivity, e.g. enhanced yield or engineered pest resistance, rely on either mutation breeding or introduction of novel genes into the genomes of crop species by transformation. Both processes are inherently nonspecific and relatively inefficient. For example, conventional plant transformation methods deliver exogenous DNA that integrates into the genome at random locations. Thus, in order to identify and isolate transgenic lines with desirable attributes, it is necessary to generate thousands of unique random-integration events and subsequently screen for the desired individuals. As a result, conventional plant trait engineering is a laborious, time-consuming, and unpredictable undertaking. Furthermore the random nature of these integrations makes it difficult to predict whether pleiotropic effects due to unintended genome disruption have occurred. As a result, the generation, isolation and characterization of plant lines with engineered genes or traits has been an extremely labor and cost-intensive process with a low probability of success.

Targeted gene modification overcomes the logistical challenges of conventional practices in plant systems, and as such has been a long-standing but elusive goal in both basic plant biology research and agricultural biotechnology. However, with the exception of "gene targeting" via positive-negative drug selection in rice or the use of pre-engineered restriction sites, targeted genome modification in all plant species, both model and crop, has until recently proven very difficult. Terada et al. (2002) *Nat Biotechnol* 20(10):1030; Terada et al. (2007) *Plant Physiol* 144(2):846; D'Halluin et al. (2008) *Plant Biotechnology J.* 6(1):93.

Creation of a targeted DSB can dramatically increase the frequency and specificity of transgene integration (Rouet, P., et al (1994) *Proc Natl Acad Sci USA*, 91: 6064-6068). The custom engineering of site-specific nucleases has therefore accelerated targeted integration technology. Zinc-finger nucleases (ZFNs) are fusions between zinc-finger DNA binding domains and the nuclease domain of the type IIs restriction enzyme FokI. When two such ZFN fusions bind at adjacent sites on the chromosome, the nuclease domains interact to create a double-strand break in the DNA. The non-homologous end-joining (NHEJ) pathway can directly ligate the broken ends together, often with a gain or loss of several base pairs (Weterings and van Gent (2004) *DNA Repair (Amst)*, 3:1425-1435).

Previous investigators have found that non-specific DNA can be captured at a site of double-strand break repair in *S. cerevisiae* (Havi-Chesnner et al, (2007) *Nucleic Acids Res,* 35, 5192-5202). In addition, repetitive element and mitochondrial DNA fragments have also been observed to integrate at the site of DSBs in *S. cerevisiae* (Moore, J. K. and Haber, J. E. (1996) *Nature,* 383, 644-646 and Yu, X. and Gabriel, A. (1999) *Mol Cell,* 4, 873-881). It is known that while many organisms, including mammals, plants and filamentous fungi tend to rely mainly on NHEJ for healing DSBs, *S. cerevisiae* is considerably more likely to use HDR for healing these lesions (Ishibashi et al, (2006) *Proc. Natl. Acad. Sci. USA* 103(40): 14871-14876). Thus it is very difficult to draw conclusions about DSB repair mechanisms in mammalian cells based on experiments performed in *S. cerevisiae*. Exogenous single-stranded oligonucleotides have been used to repair DSBs in yeast via single strand annealing (SSA) but this homology-based repair process is fundamentally different from NHEJ repair (Storici et al. (2003) *Proc Natl Acad Sci USA,* 100:14994-14999, Storici et al. (2006) *Mol Cell Biol,* 26:7645-7657).

In murine fibroblast cells, researchers were able to induce a DSB using the homing endonuclease Sce-I and found that exogenously introduced fragments from nuclease-digested φX174 genomic DNA could be captured in the break. Sequencing of the junctions revealed regions of microhomology between the two DNAs (Lin, Y. and Waldman, A. S. (2001) *Nucleic Acids Res,* 29, 3975-3981). Other experiments revealed the capture of other exogenous fragments of DNA (Lin, Y. and Waldman, A. S. (2001) *Genetics,* 158, 1665-1674). However, this result has limited practical applicability in that the researcher is bound to induction of a DSB by the Sce-I homing endonuclease and thus the location of interest must either contain a Sce-I site naturally, or the researcher must go through the arduous process of inserting a Sce-I site through random integration or some other such technique. Alternate techniques for exogenous DNA introduction rely on the practioner having extensive knowledge about the sequence identity of the region for these techniques often depend on fortuitous DSBs occurring within large stretches of homology (six or seven kilobases of DNA) between the donor and the genomic region being targeted. Recently, shorter regions of homology (50-100 bp) have been demonstrated to be functional in HDR when coupled with creation of a targeted double strand break (see co-owned U.S. Patent Publication No. 20090263900).

Therefore, to date, donor molecules have not been shown to be integrated directly into the site of cleavage. Thus, there remains a need for additional methods and compositions to allow targeted insertion of desired donor nucleic acids in cells to produce a precise, investigator-specified allele at an endogenous locus.

SUMMARY

The present disclosure provides methods and compositions for insertion of donor nucleic acid molecules into cells utilizing the non-homologous end joining (NHEJ) pathway. Specifically, the invention uses the sequence information contained in the 5' overhang in the target sequence created by nuclease cleavage to add DNA at the breakpoint and inserts DNA without undesired gain or loss of chromosomal sequence. In contrast, previous techniques involving co-transfection of fragments with blunt ends or with restriction enzyme-generated overhangs require both target and donor resection to reveal microhomology needed for fragment joining. The near impossibility of chromosomal and donor sequence conservation reduces the utility of this previous approach for directed DNA addition.

Thus, the present invention provides exogenous (donor) nucleic acids, compositions comprising these nucleic acids and methods of making and using these donor molecules. In one aspect, the donor molecules described herein contain short regions of single-stand DNA sequence complementary to the sequences flanking either side of a DSB. Generally, the donor molecules described herein are double-stranded with single-stranded complementary regions on one or both ends of the double-stranded linear nucleic acid molecule. The single strand region(s) of the donor molecule can be of any length. In certain embodiments, the single stranded region(s) is(are) between about 1 and 10 nucleotides (including 1, 2, 3, 4, 5, 6, 7, 8, 9 and 10 nucleotides in length). In some embodiments, the single strand region(s) include about 4 nucleotides, and in some embodiments, the single strand region(s) include about 5 nucleotides. In some embodiments, the single-stranded complementary region is only on one end of the linear donor molecule.

In one aspect, described herein is a linear nucleic acid molecule (donor molecule) comprising single-stranded complementary regions of about 1-10 nucleotides (i.e. 1, 2, 3, 4, 5, 6, 7, 8, 9, or 10 nucleotides) flanking a sequence of interest to be inserted. In certain embodiments, the linear donor molecule stably persists in the cell into which it is introduced. In other embodiments, the linear donor molecule is modified to resist exonucleolytic cleavage, for example by placing one or more phosphorothioate phosphodiester bonds between one or more base pairs on the ends of the donor molecule. In certain embodiments, the donor molecule comprises modified nucleotides (e.g. methylated) or non-natural nucleotide analogs at the ends or within the interior regions of the donor molecule.

The sequence of interest of the donor molecule may comprise one or more sequences encoding a functional polypeptide (e.g., a cDNA), with or without a promoter. In certain embodiments, the nucleic acid sequence comprises a sequence encoding an, antibody, an antigen, an enzyme, a growth factor, a receptor (cell surface or nuclear), a hormone, a lymphokine, a cytokine, a reporter, functional fragments of any of the above and combinations of the above. In embodiments in which the functional polypeptide encoding sequences are promoterless, expression of the integrated sequence is then ensured by transcription driven by an endogenous promoter or other control element in the region of interest. In other embodiments, a "tandem" cassette is integrated into the selected site in this manner, the first component of the cassette comprising a promoterless sequence as described above, followed by a transcription termination sequence, and a second sequence, encoding an autonomous expression cassette. Additional sequences (coding or non-coding sequences) may be included in the donor molecule between the homology arms, including but not limited to, sequences encoding a 2A peptide, SA site, IRES, etc. In certain embodiments, the donor nucleic acid comprises sequences encoding functional RNAs for example, miRNAs or shRNAs.

In some embodiments, the sequence of interest of the donor molecule may comprise one or more sequences where the sequences are non-coding sequences. In certain embodiments, the non-coding sequence comprises an integration site for a site-specific recombinase, transposase, or integrase system, for example Cre, FLP, or Sleeping Beauty recognition site. Combinations of one or more coding sequences and one or more non-coding sequences may also be included in the donor molecule. In certain embodiments, the introduced integration site is then further used to integrate other desired nucleic acids. For example, a loxP site contained on a donor nucleic acid may be introduced via the NHEJ-dependent method of the invention to a desired target location. The Cre recombinase may then be expressed in the cell to allow insertion of an additional nucleic acid of interest wherein the additional nucleic acid also contains a loxP site. In this way, the addition of the loxP site via the methods of the invention at a location of interest facilitates insertion of a wide range of nucleic acids.

In another aspect, described herein are methods of integrating a donor nucleic acid as described herein into the genome of a cell. The methods comprise creating a double-stranded break (DSB) in the genome of a cell such that the donor nucleic acid is integrated at the site of the DSB. As noted above, the donor sequences can be integrated in a targeted manner into the genome of a cell at the location of a DSB. DSBs may be created by any mechanism. In certain embodiments, the DSB is created by one or more zinc finger nucleases (ZFNs), fusion proteins comprising a zinc finger binding domain, which is engineered to bind a sequence within the region of interest, and a cleavage domain or a cleavage half-domain. In other embodiments, the DSB is created by one or more meganucleases (naturally occurring or non-naturally occurring meganuclease that have been engineered to bind to a target site). In other embodiments, the DSB is created by one or more TALE DNA binding domains (naturally occurring or non-naturally occurring) fused to a nuclease domain (TALEN).

In another aspect, provided herein is a method for integrating an exogenous sequence as described herein into a region of interest in the genome of a cell, the method comprising: (a) expressing a fusion protein in the cell, the fusion protein comprising a DNA-binding domain (e.g., zinc finger or TALE binding domain) and a cleavage domain or cleavage half-domain, wherein the DNA-binding domain (e.g., zinc finger or TALE binding domain) has been engineered to bind to a target site in the region of interest in the genome of the cell; and (b) contacting the cell with a donor polynucleotide as described herein, wherein binding of the fusion protein to the target site cleaves the genome of the cell in the region of interest, thereby resulting in integration of the exogenous sequence into the genome of the cell within the region of interest.

In certain embodiments, the methods comprise the steps of (a) expressing a first fusion protein in the cell, the first fusion protein comprising a first DNA binding domain and a first cleavage half-domain, wherein the first DNA binding domain has been engineered to bind to a first target site in the region of interest in the genome of the cell; (b) expressing a second fusion protein in the cell, the second fusion protein comprising a second DNA binding domain and a second cleavage half domain, wherein the second DNA binding domain binds to a second target site in the region of interest in the genome of the cell, wherein the second target site is different from the first target site; and (c) contacting the cell with a exogenous donor molecule comprising single strand complementary regions as described herein, wherein binding of the first fusion protein to the first target site, and binding of the second fusion protein to the second target site, positions the cleavage half-domains such that the genome of the cell is cleaved in the region of interest, thereby resulting in integration of the exogenous donor molecule into the genome of the cell within the region of interest.

In certain embodiments, the methods comprise the steps of (a) expressing a first fusion protein in the cell, the first fusion protein comprising a first DNA binding domain and a first cleavage half-domain, wherein the first DNA binding domain has been engineered to bind to a first target site in the region of interest in the genome of the cell; (b) expressing a second fusion protein in the cell, the second fusion protein comprising a second DNA binding domain and a second cleavage half domain, wherein the second DNA binding domain binds to a second target site in the region of interest in the genome of the cell, wherein the second target site is different from the first target site; and (c) expressing a third fusion protein in the cell, the third fusion protein comprising a third DNA binding domain and a third cleavage half-domain, wherein the third DNA binding domain has been engineered to bind to a third target site in the region of interest in the genome of the cell; wherein the third target site is different from the first and second target sites; and (d) expressing a fourth fusion protein in the cell, the fourth fusion protein comprising a fourth DNA binding domain and a fourth cleavage half domain, wherein the fourth DNA binding domain binds to a fourth target site in the region of interest in the genome of the cell, wherein the fourth target site is different from the first, second and third target sites; and (e) contacting the cell with a exogenous donor molecule comprising single strand complementary regions as described herein, wherein binding of the first fusion protein to the first target site, and binding of the second fusion protein to the second target site, and wherein binding of the third fusion protein to the third target site, and binding of the fourth fusion protein to the fourth target site positions the cleavage half-domains such that the genome of the cell is cleaved in the region of interest thereby resulting in integration of the exogenous donor molecule into the genome of the cell within the region of interest in lieu of the original genomic stretch, thereby creating a deletion in the genome concomitant with a replacement of that region with the donor-specified stretch.

In any of the methods described herein, the donor polynucleotide can comprise a sequence encoding a functional polypeptide, which sequence is inserted into the genome of the cell.

Furthermore, in any of the methods described herein, the first and second cleavage half-domains may be from a Type IIS restriction endonuclease, for example, FokI or StsI. Furthermore, in any of the methods described herein, at least one of the fusion proteins may comprise an alteration in the amino acid sequence of the dimerization interface of the cleavage half-domain, for example such that obligate heterodimers of the cleavage half-domains are formed. Alternatively, in any of the methods described herein the cleavage domain may be a naturally or non-naturally occurring (engineered) meganuclease.

In any of the methods described herein, the cell can be a mammalian cell, for example, a human cell. Furthermore, the cell may be arrested in the G2 phase of the cell cycle. In some embodiments of the methods described herein, the cell may be one lacking efficient homology-based DNA repair. In certain embodiments, the cells may be primary or non-dividing cells which preferentially use the NHEJ DNA repair pathway. In some embodiments, the cell can be a plant or fungal cell. In other embodiments, the methods described herein may be used in cells with unsequenced genomes.

BRIEF DESCRIPTION OF THE DRAWINGS

FIG. 1A shows a scheme to determine ZFN overhangs. A supercoiled plasmid with a ZFN cleavage site is cut by a titration of in vitro transcribed and translated ZFNs. ZFN-linearized plasmids are purified by gel electrophoresis, 5' overhangs filled in with Klenow polymerase (grey nucleotides), and the resulting blunt ends ligated. The mixture is subjected to high-throughput DNA sequencing. Panel B depicts the overhang types generated by a control restriction enzyme (HindIII) and three of the ZFN pairs used in this work. For clarity, only one DNA strand is shown. SEQ ID NO:110 shows target site designated "HindIII"; SEQ ID NO:111 shows the target site for IL2Rγ ZFNs; SEQ ID NO:112 shows the target site for GS ZFNs; and SEQ ID NO:113 shows the target site for AAVS1 ZFNs. Enzyme binding sites are shown in grey; only the flanking three nucleotides are shown for ZFN binding sites. Primary cleavage sites, black triangles; secondary and tertiary cleavage sites, dark and light grey triangles, respectively; deletions, Δ. Microhomology within the target site can prevent unambiguous deduction of the overhang type. In such situations the possible overhangs are shown as joined triangles. Either of the two indicated thymidine residues may have been deleted after HindIII digestion.

FIG. 2, panels A to D, depict targeted DNA integration via non-homologous end joining.

FIG. 3, panels A to C, depict targeted DNA integration into a deletion via non-homologous end joining.

FIG. 5, panels A to D, show capture of an oligonucleotide duplex mediated by NHEJ following cleavage by a TALEN pair. FIG. 5A is a sketch of the NTF3 target locus (top) and one of the oligonucleotide duplexes used for this study (bottom, SEQ ID NOs:94 to 97). Binding sites for NT-L+28 and NT-R+63 are underlined in the top sequence. The cleavage overhang that will most efficiently capture the duplex (5' CTGG) is also highlighted (boxed). FIG. 5B (SEQ ID NOs:98 to 101) shows a sketch of the NTF3 target locus (top) and the second oligonucleotide duplex used for this study (bottom). Binding sites for NT-L+28 and NT-R+63 are underlined in the top sequence. The cleavage overhang that will most efficiently capture this second duplex (5' TGGT) is also highlighted. FIG. 5C (SEQ ID NOs:102 to 104) shows the expected sequence following integration of the oligonucleotide duplex and sequences that were recovered following expression of the TALENs in K562 cells in the presence of the donor. It also shows the sequences of the junctions obtained in the study. FIG. 5D (SEQ ID NOs:105 to 109) shows the results using the oligonucleotide donor from FIG. 5B wherein the 4 bp overhang is shifted by one base relative to the duplex used in FIG. 5C. Shown in the bottom of FIG. 5D are the sequences obtained in this experiment which demonstrate short deletions that are consistent with resection occurring prior to NHEJ-mediated capture.

DETAILED DESCRIPTION

Figure 1:
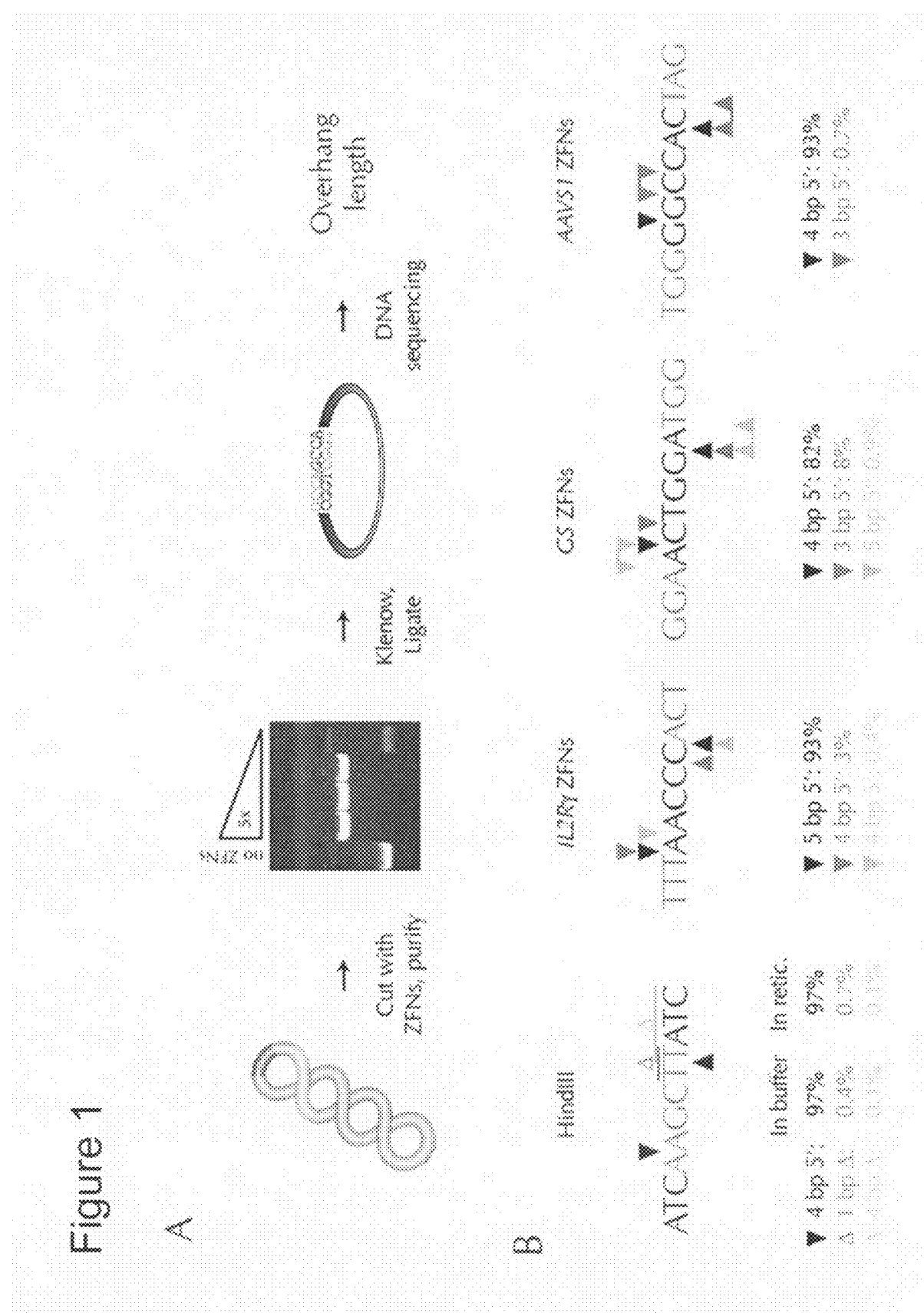
FIG. 1, panels A and B, depict analysis of the overhang types created by ZFNs.

The present disclosure relates to exogenous (donor) polynucleotides useful for targeted integration (TI) into a region of interest in a genome. In particular, the donor polynucleotides described herein are linear molecules comprising single-stranded complementary sequences that are about 1 to 10 nucleotides. The single-stranded complementary regions flank one or more sequences of interest to be inserted into the genome of a cell, typically via non-homologous end joining (NHEJ) mechanisms. These donor molecules are integrated into a specified region of interest in a genome when used in combination with fusion proteins (zinc finger or TALE nucleases) comprising a cleavage domain (or a cleavage half-domain) and a DNA binding domain (and/or polynucleotides encoding these proteins). A DNA binding domain can comprise one or more zinc fingers (e.g., 2, 3, 4, 5, 6, 7, 8, 9 or more zinc fingers), or one or more TALE DNA binding domains and can be engineered to bind to any sequence within the region of interest. In the presence of these nucleases, the linear donor polynucleotides described are integrated at high rates into the cleavage site by NHEJ-dependent methods.

Advantages of the methods and compositions described herein include the ability to use NHEJ-dependent target integration (NHEJ-based capture) in cells without homology-driven DNA repair systems, such as primary and/or non-dividing cells. Since the methods described herein rely on short (about 1-10 nucleotides) single-stranded complementary regions to allow for the targeted integration, knowledge concerning large regions of sequence identity flanking the DSB site is not needed. In contrast to homology-directed targeted integration, this insensitivity to flanking DNA (beyond the overhang created by nuclease cleavage) allows for targeted insertion into organisms that have genomes with limited knowledge of the genomic sequence. In some instances, donor molecules may be made by PCR amplification or chemical synthesis, and thus can be constructed within hours for immediate use, allowing for rapid experimentation and insertion of the nucleic acid of interest. In addition, use of linear donors as described herein reduces or eliminates the phenomena of stable maintenance of the plasmid donor by the host cell. The methods and compositions of the current invention can also be used when an exact junction is required at the site of donor insertion. This is critical when inserting coding sequences in open reading frames because it eliminates the possibility of introduction of frameshifts (often resulting in nonsense or missense alleles) mutations following donor integration.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different, protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. With respect to sequences described herein, the range of desired degrees of sequence identity is approximately 80% to 100% and any integer value therebetween. Typically the percent identities between sequences are at least. 70-75%, preferably 80-82%, more preferably 85-90%, even more preferably 92%, still more preferably 95%, and most preferably 98% sequence identity.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends: In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. An exogenous molecule can also be the same type of molecule as an endogenous molecule but be derived from a different species than the species the endogenous molecule is derived from. For example, a human nucleic acid sequence may be introduced into a cell line originating from a hamster or mouse.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Exogenous nucleic acid molecules that can be targeted for insertion into a genome are also referred to as "donor" polynucleotides. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid.

Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression, can include, but is not limited to, gene activation and gene repression.

"Eukaryotic" cells include, but are not limited to, fungal cells (such as yeast), animal cells, mammalian cells and human cells.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A "safe harbor" locus is a locus within the genome wherein a gene may be inserted without any deleterious affects on the host cell. Most beneficial is a safe harbor locus in which expression of the inserted gene sequence is not perturbed by any read-through expression from neighboring genes. Examples of safe harbor loci in mammalian cells are the AAVS1 gene (see United States Patent Publication No. 20080299580) or the CCR5 gene (see United States Patent Publication 20080159996).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

Typical "control elements" include, but are not limited to transcription promoters, transcription enhancer elements, cis-acting transcription regulating elements (transcription regulators, e.g., a cis-acting element that affects the transcription of a gene, for example, a region of a promoter with which a transcription factor interacts to modulate expression of a gene), transcription termination signals, as well as polyadenylation sequences (located 5' to the translation stop codon), sequences for optimization of initiation of translation (located 5' to the coding sequence), translation enhancing sequences, and translation termination sequences. Control elements are derived from any include functional fragments thereof, for example, polynucleotides between about 5 and about 50 nucleotides in length (or any integer therebetween); preferably between about 5 and about 25 nucleotides (or any integer therebetween), even more preferably between about 5 and about 10 nucleotides (or any integer therebetween), and most preferably 9-10 nucleotides. Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters.

A "reporter gene" or "reporter sequence" refers to any sequence that produces a protein product that is easily measured, preferably in a routine assay. Suitable reporter genes include, but are not limited to, Mel1, chloramphenicol acetyl transferase (CAT), light generating proteins such as GFP, luciferase and/or β-galactosidase. Suitable reporter genes may also encode markers or enzymes that can be measured in vivo such as thymidine kinase, measured in vivo using PET scanning, or luciferase, measured in vivo via whole body luminometric imaging. Selectable markers can also be used instead of, or in addition to, reporters. Positive selection markers are those polynucleotides that encode a product that enables only cells that carry and express the gene to survive and/or grow under certain conditions. For example, cells that express neomycin resistance (Neo$^r$) gene are resistant to the compound G418, while cells that do not express Neo$^r$ are skilled by G418. Other examples of positive selection markers including hygromycin resistance and the like will be known to those of skill in the art. Negative selection markers are those polynucleotides that encode a product that enables only cells that carry and express the gene to be killed under certain conditions. For example, cells that express thymidine kinase (e.g., herpes simplex virus thymidine kinase, HSV-TK) are killed when gancyclovir is added. Other negative selection markers are known to those skilled in the art. The selectable marker need not be a transgene and, additionally, reporters and selectable markers can be used in various combinations.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Overview

Described herein are methods and compositions for targeted integration of donor sequences into a chosen target via the NHEJ pathway. These methods use donor molecules containing one or more short single-stranded complementary regions that are complementary to the single-strand overhangs left in the target sequence following nuclease cleavage. Nucleases; such as zinc finger nucleases (ZFNs) or nucleases with TAL effector DNA domains (TALENs), cleave DNA asymmetrically, leaving mainly either 4 or 5 bp 5' overhangs depending on whether the individual nucleases bind 6 or 5 bp apart on opposite strands (Smith, J. et al, (2000) *Nucleic Acids Res*, 28:3361-3369). ZFN or TALEN pairs that bind to the target sequence with a wider gap are likely to leave longer overhangs. The methods and compositions described herein use the sequence information contained in the 5' overhang of the target sequence to add DNA to the DSB where the donor DNA is inserted without loss of chromosomal sequences surrounding the inserted sequence. In contrast, co-transfection of blunt-ended fragments requires both target and donor resection to generate regions of microhomology needed for fragment joining (Smith et al, ibid) and this resection can create unwanted or uncontrollable alterations in the target sequence. Thus, described herein are methods and compositions for targeted integration at a chosen locus using donor sequences with single-stranded complementary regions that allow for precise annealing of the donor ends with the overhang sequences left following nuclease (e.g., ZFN or TALEN) digestion, and maintenance of the chromosomal sequence information immediately adjacent to the site of insertion.

Exogenous (Donor) Polynucleotides

Described herein are methods of targeted insertion of any polynucleotides for insertion into a chosen location. Polynucleotides for insertion can also be referred to as "exogenous" polynucleotides or "donor" polynucleotides.

Surprisingly, it is demonstrated herein that linear donor sequences of the disclosure comprising short single-stranded complementary regions of approximately 1-10 nucleotides can be effectively integrated into a selected target region of the genome of cell. The single-stranded complementary regions are complementary to the overhangs left in the target sequence following nuclease digestion.

In certain embodiments, the single-stranded complementary regions described herein are about 1 to 10 nucleotides in length (or any value therebetween, including 2, 3, 4, 5, 6, 7, 8, and 9 nucleotides). In some embodiments, the single-stranded complementary region will extend from the 5' end of the top strand of the donor molecule and the 5' end of the bottom strand of the donor, creating 5' overhangs on each end of the donor molecule. In other embodiments, the single-stranded complementary region will extend from the 3' end of the top strand of the donor molecule, and the 3' end of the bottom strand of the donor, creating 3' overhangs.

The donor sequences described herein may be isolated from plasmids, cells or other sources using standard techniques known in the art such as PCR. Donors for use can varying types of topology, including circular supercoiled, circular relaxed and linear. Alternatively, they may be chemically synthesized using standard oligonucleotide synthesis techniques. In addition, donors may be methylated or lack methylation.

The linear donor polynucleotides described herein may include one or more phosphorothioate phosphodiester bonds, for example between terminal nucleotides to protect the linear donor polynucleotide from exonucleolytic degradation. These bonds may be in two or more positions at the 5' and/or 3' ends of the donor molecule and may be added during isolation or synthesis using standard methodology. See, e.g., Ciafre et al. (1995) *Nucleic Acids Res.* 23(20):4134-42; Johansson et al. (2002) *Vaccine* 20(27-28):3379-88. Alternatively, the linear donor polynucleotides may include one or more 5' deoxynucleotides, biotin and/one or more amine groups, all of which have been shown to reduce exonucleolytic degradation. Further, the donor molecules may contain non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines). In a preferred embodiment, the exogenous sequence comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g., Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In some embodiments, the donor nucleic acid includes a non-coding sequence that is target site for a specific recombinase system. Non-limiting examples include a lox P site (for use with the Cre recombinase), a FRT site (for use with the FLP recombinase) or a recognition site for a specific transposase, e.g. piggybac or Sleeping Beauty. Insertion of one of these recombinase or transposase recognition sites can allow additional insertion of nucleic acids that would be difficult to manage by traditional methods. For example, large artificial chromosomes, (YACs or BACs) could be inserted at a chosen target site of interest once the recombinase/transposase recognition site has been inserted.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Target Sites

As noted above, the donor molecule is typically integrated into the genome of the cell following cleavage of the genome in the target region. Cleavage in the target region may be accomplished using a nuclease, for example a ZFN, a TALEN, or a meganuclease. In certain embodiments, the disclosed methods make use of fusion proteins comprising a cleavage domain (or a cleavage half-domain) and a zinc finger or TALE DNA binding domain, in which the zinc finger or TALE DNA binding domain, by binding to a sequence a region of interest in the genome of a cell directs the activity of the cleavage domain (or cleavage half-domain) to the vicinity of the sequence and, hence, induces cleavage (e.g., a double stranded break) in the region of interest.

As set forth elsewhere in this disclosure, DNA binding domains such as zinc finger or TALE domains, can be engineered to bind to virtually any desired sequence. Accordingly, one or more DNA binding domains can be engineered to bind to one or more sequences in the region of interest. Expression of a fusion protein comprising a DNA binding domain and a cleavage domain (or of two fusion proteins, each comprising a DNA binding domain and a cleavage half-domain), in a cell, effects cleavage in the region of interest.

Selection of a sequence in a region of interest for binding by a DNA binding domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the methods described herein.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands. In other embodiments, both target sites are on the same DNA strand.

Choosing the location of the target site for insertion can depend on many factors. For example, in some embodiments, a target site may be chosen because of being highly characterized (for example the LCR of beta-globin) while in other embodiments, a target site is selected due to its characteristics as a safe harbor locus (for example the CCR5 or AAVS1 gene, see United States Patent Publications No: 20080159996 and 20080299580, respectively).

DNA Binding Domains

Any DNA-binding domain can be used in the methods disclosed herein. In certain embodiments, the DNA-binding domain comprises a TALE DNA binding domain. In other embodiments, the DNA binding domain comprises a zinc finger protein. A zinc finger binding domain comprises one or more zinc fingers. Miller et al. (1985) *EMBO J.* 4:1609-1614; Rhodes (1993) *Scientific American February*:56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293.

Zinc finger binding domains can be engineered to bind to a target site (see above) using standard techniques. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; co-owned U.S. Pat. Nos. 6,453,242 and 6,534,261, including references cited therein. An engineered zinc finger binding domain can have a novel binding specificity, compared to a naturally-occurring zinc finger protein. Generally, a non-naturally occurring engineered recognition helix region provides the novel binding specificity. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. Examples of additional linker structures are found in U.S. Patent Publication 2009/0305419.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are, not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In some embodiments, the DNA binding domain is an engineered domain from a TAL effector (TALE) derived from the plant pathogen *Xanthomonas* (see, Miller et al. (2010) *Nature Biotechnology*, December 22 [Epub ahead of print]; Boch et al, (2009) *Science* 29 Oct. 2009 (10.1126/science.117881) and Moscou and Bogdanove, (2009) *Science* 29 Oct. 2009 (10.1126/science.1178817); see, also, U.S. Provisional Application Nos. 61/395,836, filed May 17, 2010; 61/409,421, filed Aug. 21, 2010; 61/45,121, filed Oct. 13, 2010; 61/459,891, filed Dec. 20, 2010 and Application No. Unassigned, filed Feb. 2, 2011, the disclosures of which are hereby incorporated by reference in their entireties.

In certain embodiments, a four-, five-, or six-finger zinc finger binding domain as is fused to a cleavage half-domain, such as, for example, the cleavage domain of a Type IIs restriction endonuclease such as FokI. One or more pairs of such zinc finger/nuclease half-domain fusions are used for targeted cleavage, as disclosed, for example, in U.S. Patent Publication Nos. 20050064474 and 20070218528.

For targeted cleavage, the near edges of the binding sites can separated by 5 or more nucleotide pairs, and each of the fusion proteins can bind to an opposite strand of the DNA target. Following the present disclosure, ZFNs can be targeted to any sequence of any gene in the selected cell, including for example CCR5, PPP1R12c (also known as AAV S1) as well as others. See, International Patent Publication WO/2008/133938 and U.S. Patent Publication No. 2008015996 describing ZFNs targeted to CCR5 and AAV S1, incorporated by reference herein. In certain embodiments, the ZFNs are targeted to a "non-essential" gene in that targeted integration into that site does not interfere with the cells ability to proliferate and/or differentiate.

Cleavage Domains

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in co-owned International Publication WO 2007/014275, incorporated by reference herein in its entirety. Additional restriction enzymes also contain separable binding and cleavage domains, and these are contemplated by the present disclosure. See, for example, Roberts et al. (2003) *Nucleic Acids Res.* 31:418-420.

To enhance cleavage specificity, cleavage domains may also be modified. In certain embodiments, variants of the cleavage half-domain are employed, which variants that minimize or prevent homodimerization of the cleavage half-domains. Non-limiting examples of such modified cleavage half-domains are described in detail in WO 2007/014275, incorporated by reference in its entirety herein. See, also, Examples. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474; 20060188987; 20080131962; 20090305346 and U.S. Provisional Application Nos. 61/337,769, filed Feb. 8, 2010 and 61/403,916, filed Sep. 23, 2010, incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Additional engineered cleavage half-domains of Fok I form an obligate heterodimers can also be used in the ZFNs described herein. The first cleavage half-domain includes mutations at amino acid residues at positions 490 and 538 of Fok I and the second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (O) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". As described in the examples a pair of ZFNs in which one ZFN comprises the "E490K:I538K" cleavage domain and other comprises "Q486E:I499L" cleavage domain is also referred to as a "EL/KK" ZFN pair. The engineered cleavage half-domains described herein are obligate heterodimer mutants in which aberrant cleavage is minimized or abolished when one or more pairs of nucleases containing these cleavage half-domains are used for cleavage. See, e.g., U.S. Patent Publication Nos. 20080131962; 20090305346 and U.S. Provisional Application Nos. 61/337,769, filed Feb. 8, 2010 and 61/403,916, filed Sep. 23, 2010, the disclosures of which is incorporated by reference in their entireties for all purposes.

Engineered cleavage half-domains described herein can be prepared using any suitable method, for example, by site-directed mutagenesis of wild-type cleavage half-domains (Fok I) as described in U.S. Patent Publication Nos. 20050064474 (Example 5) and 20070134796 (Example 38).

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

DNA-Binding Domain-Cleavage Domain Fusions

Methods for design and construction of fusion proteins (and polynucleotides encoding same) are known to those of skill in the art. For example, methods for the design and construction of fusion protein comprising zinc finger proteins (and polynucleotides encoding same) are described in co-owned U.S. Pat. Nos. 6,453,242 and 6,534,261; and International Publication WO 2007/014275. In certain embodiments, polynucleotides encoding such fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a fusion protein comprises a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

Two fusion proteins, each comprising a zinc finger or TALE DNA binding domain and a cleavage half-domain, may be expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger or TALE DNA binding domains. One or both of the zinc finger or TALE DNA binding domains and/or cleavage domains can be engineered.

The components of the fusion proteins (e.g., ZFP-Fok I fusions) may be arranged such that the zinc finger or TALE DNA binding domain is nearest the amino terminus of the fusion protein, and the cleavage half-domain is nearest the carboxy-terminus. Dimerization of the cleavage half-domains to form a functional nuclease is brought about by binding of the fusion proteins to sites on opposite DNA strands, with the 5' ends of the binding sites being proximal to each other.

Alternatively, the components of the fusion proteins (e.g., ZFP-Fok I or TALEN fusions) may be arranged such that the cleavage half-domain is nearest the amino terminus of the fusion protein, and the zinc finger or TALE DNA binding domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger or TALE DNA binding domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger or TALE DNA binding domain nearest the carboxy terminus located to the 5' side of the binding site of the second fusion protein containing the zinc finger or TALE DNA binding domain nearest the amino terminus.

The two fusion proteins can bind in the region of interest in the same or opposite polarity, and their binding sites (i.e., target sites) can be separated by any number of nucleotides, e.g., from 0 to 200 nucleotides or any integal value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for targeted integration, cleavage within a range of nucleotides is generally sufficient, and cleavage between particular base pairs is not required.

In the disclosed fusion proteins, the amino acid sequence between the zinc finger domain and the cleavage domain (or cleavage half-domain) is denoted the "ZC linker." The ZC linker is to be distinguished from the inter-finger linkers discussed above. ZC linkers are described in detail, for example, in WO 2007/014275.

Targeted Integration

The disclosed methods and compositions can be used to cleave DNA in cellular chromatin, which facilitates targeted integration of an exogenous sequence (donor polynucleotide) as described herein. For targeted integration, one or more zinc finger or TALE DNA binding domains are engineered to bind a target site at or near the predetermined cleavage site, and a fusion protein comprising the engineered zinc finger or TALE DNA binding domain and a cleavage domain is expressed in a cell. Upon binding of the zinc finger or TALE DNA binding portion of the fusion protein to the target site, the DNA is cleaved, preferably via a double stranded break, near the target site by the cleavage domain. The presence of a double-stranded break facilitates integration of exogenous sequences as described herein via NHEJ mechanisms.

Targeted integration of exogenous sequences, as disclosed herein, can be used to generate cells and cell lines for protein expression. See, for example, co-owned U.S. Patent Application Publication No. 2006/0063231 (the disclosure of which is hereby incorporated by reference herein, in its entirety, for all purposes). For optimal expression of one or more proteins encoded by exogenous sequences integrated into a genome, the chromosomal integration site should be compatible with high-level transcription of the integrated sequences, preferably in a wide range of cell types and developmental states. However, it has been observed that transcription of integrated sequences varies depending on the integration site due to, among other things, the chromatin structure of the genome at the integration site. Accordingly, genomic target sites that support high-level transcription of integrated sequences are desirable. In certain embodiments, it will also be desirable that integration of exogenous sequences not result in ectopic activation of one or more cellular genes (e.g., oncogenes). On the other hand, in the case of integration of promoter and/or enhancer sequences, ectopic expression may be desired.

The exogenous (donor) sequence can be introduced into the cell prior to, concurrently with, or subsequent to, expression of the fusion protein(s).

Methods and compositions are also provided that may enhance levels of targeted modification including, but not limited to, the use of additional ZFP-functional domain fusions. See, WO 2007/014275.

Further increases in efficiency of targeted modification, in cells comprising a zinc finger or TALE/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP or TALE which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Delivery

The nucleic acids as described herein (e.g., a polynucleotide encoding ZFN and/or donor sequence) may be introduced into a cell using any suitable method. Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Similarly, the fusion protein(s) (e.g., TALENs or ZFNs) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides, is introduced into a cell. Polynucleotides can be DNA, RNA or any modified forms or analogues or DNA and/or RNA.

In certain embodiments, one or more fusion proteins can be cloned into a vector for transformation into prokaryotic or eukaryotic cells for replication and/or expression. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more nuclease encoding sequences and/or one or more sequences of interest. For example, when one or more pairs of nucleases are introduced into the cell, the nucleases may be carried on the same vector or on different vectors. When multiple vectors are used, each vector may comprise a sequence encoding one or multiple nucleases and/or one or multiple reporter constructs.

A nucleic acid encoding sequences described herein (ZFNs or TALENs) can also be cloned into an expression vector, for administration to a plant cell, animal cell, preferably a mammalian cell or a human cell, fungal cell, bacterial cell, or protozoal cell. Suitable bacterial and eukaryotic promoters are well known in the art and described, e.g., in Sambrook et al., Molecular Cloning, A Laboratory Manual (2nd ed. 1989;

3rd ed., 2001); Kriegler, Gene Transfer and Expression: A Laboratory Manual (1990); and Current Protocols in Molecular Biology (Ausubel et al., supra. Bacterial expression systems for expressing the ZFP are available in, e.g., *E. coli*, *Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a fusion protein-encoding nucleic acid depends on the particular application. For example, a strong constitutive promoter suited to the host cell is typically used for expression and purification of fusion proteins.

In contrast, when a fusion protein is administered in vivo for regulation of a plant gene (see, "Nucleic Acid Delivery to Plant Cells" section below), either a constitutive, regulated (e.g., during development, by tissue or cell type, or by the environment) or an inducible promoter is used, depending on the particular use of the fusion protein. Non-limiting examples of plant promoters include promoter sequences derived from *A. thaliana* ubiquitin-3 (ubi-3) (Callis, et al., 1990, *J. Biol. Chem.* 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., 1996, *Plant Molecular Biology* 31:1129-1139).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the fusion protein, and signals required, e.g., for efficient polyadenylation of the transcript, transcriptional termination, ribosome binding sites, or translation termination. Additional elements of the cassette may include, e.g., enhancers, heterologous splicing signals, and/or a nuclear localization signal (NLS).

The particular expression vector used to transport the genetic information into the cell is selected with regard to the intended use of the fusion proteins, e.g., expression in plants, animals, bacteria, fungus, protozoa, etc. Standard bacterial and animal expression vectors are known in the art and are described in detail, for example, U.S. Patent Publication 20050064474A1 and International Patent Publications WO05/084190, WO05/014791 and WO03/080809.

In certain embodiments, the nucleases and donor sequences are delivered in vivo or ex vivo in cells (e.g. mammalian cells) and target tissues for gene therapy uses. Such methods can also be used to administer such nucleic acids to stem cells in vitro. Non-viral vector delivery systems for delivering polynucleotides to cells include DNA plasmids, naked nucleic acid, and nucleic acid complexed with a delivery vehicle such as a liposome or poloxamer. Viral vector delivery systems for delivery of the ZFNs include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene. Therapy* 1:13-26 (1994), incorporated by reference herein.

Methods of non-viral delivery of nucleic acids in vivo or ex vivo include electroporation, lipofection (see, U.S. Pat. Nos. 5,049,386; 4,946,787 and commercially available reagents such as Transfectam™ and Lipofectin™), microinjection, biolistics, virosomes, liposomes (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787), immunoliposomes, polycation or lipid:nucleic acid conjugates, naked DNA, artificial virions, viral vector systems (e.g., retroviral, lentivirus, adenoviral, adeno-associated, vaccinia and herpes simplex virus vectors as described in WO 2007/014275 for delivering proteins comprising ZFPs) and agent-enhanced uptake of DNA. Sonoporation using, e.g., the Sonitron 2000 system (Rich-Mar) can also be used for delivery of nucleic acids. In addition, mRNAs encoding the engineered ZFPs may also be delivered to the cells by any suitable means known in the art.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.) and Copernicus Therapeutics Inc., (see for example U.S. Pat. No. 6,008,336).

Lipofection is described in for example, U.S. Pat. No. 5,049,386; U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs or TALEs takes advantage of highly evolved processes, for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In certain embodiments, the nucleic acids (e.g., encoding the ZFNs) are delivered using viral vectors such as lentiviral vectors. Viral vectors may be used to deliver the donor nucleic acids as well if the donor is flanked by the ZFN or other nuclease target sites that would allow for the generation of a linear donor molecule with single stranded overhangs that are compatible with those at the integration site following nuclease cleavage. Lentiviral transfer vectors can be produced generally by methods well known in the art. See, e.g., U.S. Pat. Nos. 5,994,136; 6,165,782; and 6,428,953. Preferably, the lentivirus donor construct is an integrase deficient lentiviral vector (IDLV). IDLVs may be produced as described, for example using lentivirus vectors that include one or more mutations in the native lentivirus integrase gene, for instance as disclosed in Leavitt et al. (1996) *J. Virol.* 70(2):721-728; Philippe et al. (2006) *Proc. Nat'l Acad. Sci. USA* 103(47):17684-17689; and WO 06/010834. In certain embodiments, the IDLV is an HIV lentiviral vector comprising a mutation at position 64 of the integrase protein (D64V), as described in Leavitt et al. (1996) *J. Virol.* 70(2):721-728. Additional IDLV vectors suitable for use herein are described in U.S. Patent Publication'No. 20090117617, incorporated by reference herein.

In certain embodiments, for example, in which transient expression of a fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many applications, it is desirable that the vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells or stem cells into the host organism) is well known to those of skill in the art. In a preferred embodiment, cells are isolated from the subject organism, transfected with a ZFP nucleic acid (gene or cDNA) and exogenous sequence, and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.*, 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)). In addition, induced pluripotent stem cells (iPSC) may also be utilized.

Vectors (e.g., retroviruses, adenoviruses, liposomes, etc.) comprising nucleic acids as described herein can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, one or more of fusion proteins can be also be introduced into the cell as polypeptides using methods described for example in WO 2007/014275. Non-limiting examples of protein delivery vehicles include, "membrane translocation polypeptides," for example peptide have amphiphilic or hydrophobic amino acid subsequences that have the ability to act as membrane-translocating carriers, toxin molecules, liposomes and liposome derivatives such as immunoliposomes (including targeted liposomes).

Nucleases, donors and expression vectors comprising these nucleases and/or donors can be administered directly to the patient for targeted cleavage and integration into a desired locus, for example the PPP1R12c locus, for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. (See co-owned United States Patent Publication No: 20080299580)

Administration of therapeutically effective amounts is by any of the routes normally used for introducing fusion proteins into ultimate contact with the tissue to be treated. The proteins are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., *Remington's Pharmaceutical Sciences,* 17$^{th}$ ed. 1985)).

The fusion proteins, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium* T-DNA delivery may be used to deliver the donor nucleic acids if the donor is flanked by the ZFN or other nuclease target sites that allow for the generation of a linear donor molecule with single stranded overhangs that are compatible with those at the integration site following nuclease cleavage. *Agrobacterium tumefaciens*-mediated transformation techniques, including disarming and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer as discussed above may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al. (1985) *Science* 227:1229-1231). Generally, the *Agrobacterium* transformation system is used to engineer dicotyledonous plants (Bevan et al. (1982) *Ann. Rev. Genet.* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J.* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into the multiple insertion site that has been inserted into the genome of a plant cell. This is useful inasmuch as expression of an introduced transgene into a plant genome depends critically on its integration site. Accordingly, genes encoding, e.g., herbicide tolerance, insect resistance, nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera Asparagus, *Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the (3-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product, In addition, the levels of polypeptide expressed can be measured immunochemically, i.e., ELISA, RIA, EIA and other antibody based assays well known to those of skill in the art, such as by electrophoretic detection assays (either with staining or Western blotting). As one non-limiting example, the detection of the AAD-1 and PAT proteins using an ELISA assay is described in U.S. patent application Ser. No. 11/587,893 which reference is hereby incorporated by reference in its entirety herein. The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs or TALENs) and expression vectors encoding fusion proteins can be administered directly to the plant for gene regulation, targeted cleavage, and/or recombination. In certain embodiments, the plant contains multiple paralogous target genes. It is known that plants may contain multiple paralogous genes. Thus, one or more different fusion proteins or expression vectors encoding fusion proteins may be administered to a plant in order to target one or more Zp15 genes in the plant.

Administration of effective amounts is by any of the routes normally used for introducing fusion proteins into ultimate contact with the plant cell to be treated. The fusion proteins are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

Applications

The disclosed methods and compositions can be used for targeted integration of any sequence into a cell wherein the targeted integration is achieved via the NHEJ pathway. Unlike homology directed repair (HDR)-mediated gene addition, donor capture by NHEJ as described herein results in the direct incorporation of the donor (exogenous) DNA into the chromosome. Additionally, capture (integration) occurs without the reliance on extensive sequence information for the target site. Also, since the donor DNAs are directly captured, use of phosphorothioate donors therefore can result in the chromosomal insertion of chemically abnormal DNA. One notable potential use for the NHEJ capture technique is the creation of cells with a variety of non-native DNA bases and backbones. In particular, insertion of DNA with methylated cytosines could serve to establish an area of transcriptional quiescence. Targeted integration of oligonucleotide donors can be used for epitope tagging, for the creation or modification or transcription factor binding sites or for insertion of sites regulating RNA splicing.

Synthetic donors containing recombinase recognition sequences, (such as loxP sites) can be used with Cre-mediated transgene integration at such sites. Such a strategy could be used to replace the deleted regions with variants of the original gene, allowing study of isolated haplotypes, or to integrate any desired nucleic acid into a desired location. For example, any transgene too large to be efficiently cloned in bacteria or integrated via HDR might be better integrated via a two-step recombinase-mediated process. For example, a yeast artificial chromosome donor functionalized with a loxP site could be site-specifically integrated after transfection (Marschall et al (1999) *Gene Ther*, 6, 1634-1637). Additionally, the insertion of such a recognition site would allow for the production of a cell which could be used to integrate a variety of differing donors via the same recognition site. By way of example, this could be useful for constructing proprietary or high producer cell lines for recombinant protein production.

NHEJ-mediated targeted integration is a preferred method for insertion of any nucleic acid when the HDR system is not readily usable. Non-limiting examples include allowing for targeted integration into non-dividing cells, primary cells, and cells which perform homology-based DNA repair poorly. The flexibility of ZFN or TALEN design and the speed at which linear donor as described herein can be created will accelerate targeted transgene integration into mammalian genomes. Finally, the directed capture of exogenous DNA should prove extensible to DSBs created by other nucleases (such as meganucleases) which leave defined overhangs amenable to rational donor design.

EXAMPLES

Example 1

Preparation of ZFNS

ZFNs targeted to AAVS1, GS, BAK, POU5F1 and IL2Rγ were designed and incorporated into plasmids or adenoviral vectors essentially as described in Urnov et al. (2005) *Nature* 435(7042):646-651, Perez et al (2008) *Nature Biotechnology* 26(7): 808-816, and U.S. Patent Publication 2008/0131962. In addition, see United States patent publication US20080299580 for ZFNs targeted to AAVS1 and United States patent publication corresponding to U.S. Patent Publication No. 20100129869 for ZFNs targeted to GS.

The recognition helices for representative ZFN designs are shown below in Table 1. Target sites of the zinc-finger designs are shown in the first column. Nucleotides in the target site that are contacted by the ZFP recognition helices are indicated in uppercase letters; non-contacted nucleotides indicated in lowercase.

TABLE 1

| ZFN Name (gene) | F1 | F2 | F3 | F4 | F5 | F6 |
|---|---|---|---|---|---|---|
| ZFN 15556 (AAVS1) | YNWHLQR (SEQ ID NO: 1) | RSDHLTT (SEDQ ID NO: 2) | HNYARDC (SEQ ID NO: 3) | QNSTRIG (SEQ ID NO: 4) | N/A | N/A |
| ZFN 15590 (AAVS1) | QSSNLAR (SEQ ID NO: 5) | RTDYLVD (SEQ ID NO: 6) | YNTHLTR (SEQ ID NO: 7) | QGYNLAG (SEQ ID NO: 8) | N/A | N/A |
| ZFN 9075 (GS) | QSSDLSR (SEQ ID NO: 9) | RSDNLRE (SEQ ID NO: 10) | RSDTLSN (SEQ ID NO: 11) | RKDVRIT (SEQ ID NO: 12) | N/A | N/A |
| ZFN 9372 (GS) | RSDHLST (SEQ ID NO: 13) | QSSDLRR (SEQ ID NO: 14) | RSDHLSQ (SEQ ID NO: 15) | QSANRTT (SEQ ID NO: 16) | RSDNLSQ (SEQ ID NO: 17) | ASNDRKK (SEQ ID NO: 18) |
| ZFN 16245 (POU5F1) | DRSALSR (SEQ ID NO: 19) | RSDALAR (SEQ ID NO: 20) | RSDVLSE (SEQ ID NO: 21) | TSGHLSR (SEQ ID NO: 22) | QSSDLRR (SEQ ID NO: 14) | N/A |
| ZFN 16246 (POU5F1) | DRSHLSR (SEQ ID NO: 23) | QSGNLAR (SEQ ID NO: 24) | RSDALSA (SEQ ID NO: 25) | NRSDRTR (SEQ ID NO: 26) | N/A | N/A |
| ZFN 16247 (POU5F1) | NSDHLTN (SEQ ID NO: 27) | DRANLSR (SEQ ID NO: 28) | RSDNLSV (SEQ ID NO: 29) | QNATRIN (SEQ ID NO: 30) | QSGSLTR (SEQ ID NO: 31) | N/A |
| ZFN 16248 (POU5F1) | RSDHLSA (SEQ ID NO: 32) | DRSNRKT (SEQ ID NO: 33) | RSAALSR (SEQ ID NO: 34) | QSADRTK (SEQ ID NO: 35) | RSANLTR (SEQ ID NO: 36) | N/A |
| ZFN 10317 (BAK del. A) | RSDNLAR (SEQ ID NO: 37) | RSDNLTT (SEQ ID NO: 38) | QSSNLAR (SEQ ID NO: 5) | RSDNLRE (SEQ ID NO: 10) | N/A | N/A |
| ZFN 11183 (BAK) | RSDHLSE (SEQ ID NO: 39) | QNHHRIN (SEQ ID NO: 40) | RSDNLRE (SEQ ID NO: 10) | ERGTLAR (SEQ ID NO: 41) | RSDNLRE (SEQ ID NO: 10) | N/A |
| ZFN 11177 (BAK del. B) | QSGHLAR (SEQ ID NO: 42) | RSDALTQ (SEQ ID NO: 43) | RSDNLTR (SEQ ID NO: 44) | RSDHLSV (SEQ ID NO: 45) | TRSNRTT (SEQ ID NO: 82) | N/A |
| ZFN 10311 (BAK) | RSDNLSE (SEQ ID NO: 46) | ASKTRKN (SEQ ID NO: 47) | RSDHLSE (SEQ ID NO: 39) | TSSDRTK (SEQ ID NO: 48) | N/A | N/A |
| ZFN 10344 (BAK) | QSSDLSR (SEQ ID NO: 9) | RSDNLTR (SEQ ID NO: 44) | QRSNLVR (SEQ ID NO: 49) | RSDNLRE (SEQ ID NO: 10) | N/A | N/A |
| ZFN 10342 (BAK) | RSDTLSV (SEQ ID NO: 50) | DNSTRIK (SEQ ID NO: 51) | RSDALSV (SEQ ID NO: 52) | DSSHRTR (SEQ ID NO: 53) | N/A | N/A |

TABLE 1-continued

Zinc-finger Designs

| ZFN Name (gene) | F1 | F2 | F3 | F4 | F5 | F6 |
|---|---|---|---|---|---|---|
| ZFN 7263 (IL2Rγ) | RSDNLSV (SEQ ID NO: 29) | RNAHRIN (SEQ ID NO: 83) | RSDTLSE (SEQ ID NO: 84) | ARSTRTN (SEQ ID NO: 85) | N/A | N/A |
| ZFN 7264 (IL2Rγ) | RSDTLSE (SEQ ID NO: 84) | ARSTRTT (SEQ ID NO: 86) | RSDSLSK (SEQ ID NO: 87) | QRSNLKV (SEQ ID NO: 88) | N/A | N/A |

TABLE 2

Zinc Finger Target Sequences

| ZFN Name (gene) | target sequence |
|---|---|
| ZFN 15556 (AAVS1) | ccCCACTGTGGGGTggaggggacagta (SEQ ID NO: 54) |
| ZFN 15590 (AAVS1) | acTAGGGACAGGATgtgttcacagtca (SEQ ID NO: 55) |
| ZFN 9075 (GS) | gaATGGTGCAGGCTgccataccaactttt (SEQ ID NO: 56) |
| ZFN 9372 (GS) | gtTCCCAGGAATGGGCTTGGggtcaaag (SEQ ID NO: 57) |
| ZFN 16245 (POU5F1) | aaGCTGGTCTGGTGGCTaggtagatcct (SEQ ID NO: 58) |
| ZFN 16246 (POU5F1) | ggGCTCTGGAAGGCccacttcagggcct (SEQ ID NO: 59) |
| ZFN 16247 (POU5F1) | atGTAACAAAGGACTACtcttcccccag (SEQ ID NO: 60) |
| ZFN 16248 (POU5F1) | atGAGTCAGTGAACAGGgaatgggtgaa (SEQ ID NO: 61) |
| ZFN 10317 (BAK del. A) | gcCAGGATTAGGAGgatgggatttggca (SEQ ID NO: 62) |
| ZFN 11183 (BAK) | caCGGGCCCAGGGTGGGgcagaaagccc (SEQ ID NO: 63) |
| ZFN 11177 (BAK del. B) | agGATTAGGAGgATGGGAtttggcactg (SEQ ID NO: 64) |
| ZFN 10311 (BAK) | caGCACGGGCCCAGggtggggcagaaag (SEQ ID NO: 65) |
| ZFN 10344 (BAK) | atCAGGAAGAGGCTgggtgtcacagcgt (SEQ ID NO: 66) |
| ZFN 10342 (BAK) | gcGGCCAGGCCAAGgcagactttctgac (SEQ ID NO: 67) |
| ZFN 7263 (IL2Rγ) | cACTCTGTGGAAGt (SEQ ID NO: 89) |
| ZFN 7264 (IL2Rγ) | ttAAAGCGGCTCCGaa (SEQ ID NO: 90) |

Example 2

NHEJ Driven Donor Capture in AAVS1

ZFNs cleave DNA asymmetrically, leaving mainly either 4 or 5 bp 5' overhangs depending on whether the individual ZFNs bind 6 or 5 bp apart on opposite strands (Smith et al. (2000) *Nucleic Acids Res*, 28:3361-3369). Since Smith's report, ZFNs with different designs have been developed. Thus, a simple assay to measure ZFN cleavage overhangs was devised.

In brief, a ZFN-cleaved target plasmid was purified, treated with Klenow polymerase to create blunt-ended fragments, the fragments ligated in cis, and the ligated region sequenced (FIG. 1A). This procedure yielded short duplications between the ZFN binding sites from which the identity of the overhangs can be deduced: To create the ZFN target plasmid, oligos containing ZFN target sites for the AAVS1 (5'-tgt ccc ctc cAC CCC ACA GTG Ggg cca cTA GGG ACA GGA Ttg gtg aca ga-3', SEQ ID NO:91), GS (5'-gac cCC AAG CCC ATT CCT GGG Aac tgg aAT GGT GCA GGC Tgc cat acc aa-3', SEQ ID NO:92), and IL2Rγ (5'-gtt tcg tgt tCG GAG CCG CTT Taa ccc ACT CTG TGG AAG tgc tca gca tt-3', SEQ ID NO:93) ZFN pairs were annealed to their reverse complements in 50 mM NaCl, 10 mM Tris pH 7.5, and 1 mM EDTA. Capital letters denote the ZFN binding sites while lowercase letters denote flanking and spacer sequence.

The double-stranded products were then cloned into the EcoRV site of the pBluescript II KS (Stratagene). ZFNs were synthesized in vitro by means of a T7-coupled transcription/translation kit using rabbit reticulocyte lysate (Promega). For the 2A-linked ZFNs AAVS1 (SBS15556 and 15590) and GS (SBS 9372 and 9075), 30 ng of plasmid were used; for the unlinked IL2Rγ ZFNs (SBS 7263 and 7264), 20 ng of each plasmid were used. Transcription and translation reactions (60 µL) were supplemented with 500 µM ZnCl$_2$ and incubated for 1.5 hours at 30° C. ZFN-containing lysates were used for DNA cleavage within 30 minutes. With the exception of those targeting IL2Rγ, all ZFNs used were of the HiFi variety (Miller et al, (2005) *Nature*, 435, 646-651).

Cleavage reactions (35 µL) contained 2.5 µg of target plasmid, 28.5 µL of reticulocyte lysate, 10 mM EGTA, and 1× Restriction Buffer 2 (New England Biolabs) and were incubated at 37° C. Control experiments with HindM in ZFN-free lysate, and Hind III in 1×NEB Buffer 2 were also conducted. Plasmid linearization required the presence of the correct ZFN pair. Reactions with AAVS1, IL2Rγ, and HindIII were terminated after 2 minutes and the GS reaction after 5 minutes by addition of 10 mM Tris/1 mM EDTA to 200 µL, followed by phenol extraction and ethanol precipitation. Linearized plasmids were gel purified by agarose gel electrophoresis and incubated for 30 min at 37° C. with 0.05 U Klenow DNA polymerase (New England Biolabs) in 1× Buffer 2, plus 50 µM dNTPs. Klenow polymerase was inactivated by incubation at 75° C. for 20 minutes, followed by addition of 20 U of T4 DNA Ligase (New England Biolabs) and ATP to 1 mM.

Ligation reactions were amplified with 30 cycles of PCR using target-specific primers containing standard Illumina sequencing regions. PCR products were purified with the QIAquick Gel Extraction Kit, then re-purified with a Gene-JET PCR Purification Kit (Fermentas), and eluted in 0.1× elution buffer. Samples were mixed together at an equimolar ratio and submitted for 34 bp read length Illumina DNA sequencing (Elim Biopharmaceuticals). Sequencing reads with a quality score of at least 30 were binned using a custom Python script. A quality score cutoff of 2 was used for AAVS1 reads due to a template-specific sequencing anomaly that reduced quality scores without an actual adverse effect on sequence interpretability. Wild-type target sequences (5-15% of the total) were discarded and the top 10 bins for each target were analyzed manually. Percentages given in the text were calculated using the relevant bin as the numerator and the entire collection of reads as the denominator. The percentages shown do not sum to 100% as the unanalyzed sequences (1500 bins with 0.2-0.0001% each) were not analyzed. For HindIII in buffer 2,573490 sequence reads were analyzed; for HindIII in reticulocyte lysate, 3473683; for IL2Rγ, 1985413; for GS, 2389486; AAVS1, 3111505.

The use of high-throughput DNA sequencing allowed the full spectrum of cleavage products to be revealed. This strategy was validated by measuring the 4 bp 5' overhangs generated by the well-characterized HindIII restriction enzyme, and then was used to determine the overhangs created by the IL2Rγ, GS, and AAVS1 zinc-finger nucleases (FIG. 1B). For IL2Rγ where the ZFN monomers are 5 bp apart, 5 bp 5' overhangs comprised 93% of all overhang types. Secondary and tertiary classes of 4 bp overhangs were seen due to 1 bp shifts in the top and bottom strand nicking sites. Analogous results were obtained for GS and AAVS1: these 6 bp-spaced ZFNs produced predominantly 4 bp overhangs with secondary products generated from 1 bp shifts in the FokI nuclease cleavage. Importantly, cleavage in reticulocyte lysate had no effect on the types of overhangs generated (FIG. 1B).

Two 49 bp 5' phosphorylated oligonucleotides designed to have 4 bp 5' overhangs complementary to those produced by the AAVS1 ZFNs when annealed (diagramed in FIG. 2A) were synthesized. Double-stranded oligonucleotides for direct insertion into the chromosome were annealed in 50 mM NaCl, 10 mM Tris pH 7.5, and 1 mM EDTA at a final concentration of 40 or 500 uM each (FIGS. 2 and 3, respectively).

Correct annealing was verified by non-denaturing polyacrylamide gel electrophoresis. Oligonucleotides used are shown below in Table 3. These oligonucleotides contain EcoRI and BamHI restriction enzyme recognition sites (indicated by underlining in Table 3). These oligonucleotides, identical versions lacking the first four bases, and versions with the first four bases changed to 5'-ctgg-3' and 5'-ccag-3', respectively were used as donors in FIG. 2B.

Figure 2A:
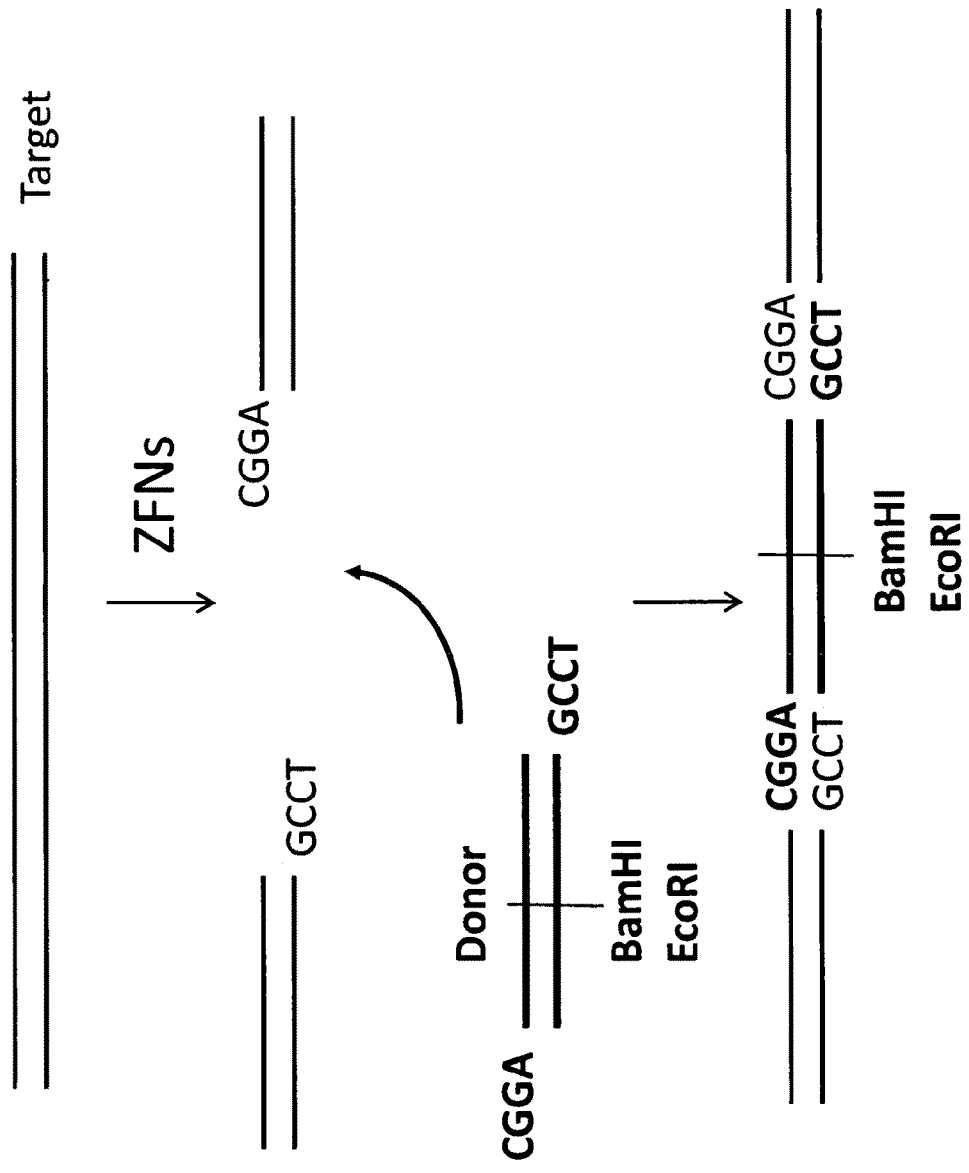
FIG. 2A depicts a diagram of ZFN cleavage at the AAVS1 locus resulting in 4 bp 5' overhangs followed by in vivo ligation of a complementary-overhang donor. The donor contains both BamHI and EcoRI restriction enzyme sites.
Figure 2B:
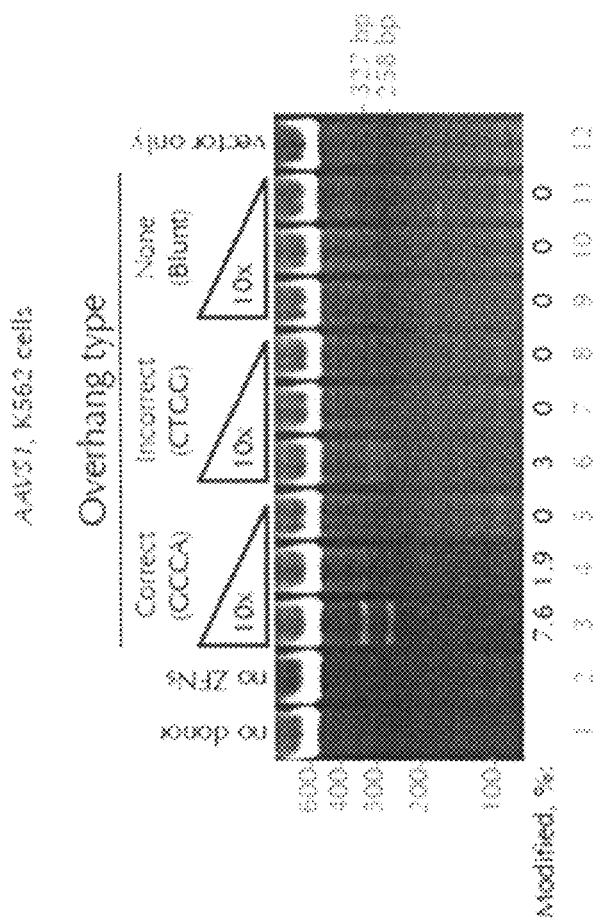
FIG. 2B shows results of a PCR-based RFLP knock in (Urnov et al (2005) *Nature.* 435(7042):646-651) assay measuring NHEJ-based capture at the AAVS1 locus in K562 cells. Three ten-fold dilutions of donor DNA with the indicated overhang types were co-transfected with the AAVS1 ZFNs. All donors in this experiment contained terminal phosphorothioate residues.

These double-stranded DNA donors were co-transfected with the AAVS1 ZFNs. For donor capture by NHEJ, one million K562 cells, 3 μg 2A-linked AAVS1 ZFNs, and 2000, 200, 20, or 0 nM donor were transfected in 100 μL. Two days post-transfection, the AAVS1 locus was amplified by PCR and donor insertion into the AAVS1 site assayed by EcoRI digestion (FIG. 2B). All PCR reactions done for analysis of donor capture by NHEJ contained 100 ng genomic DNA, 1× Accuprime Buffer II, and 1 U Accuprime Taq DNA Polymerase High Fidelity (Invitrogen), and 50 uM each of the appropriate primer. PCR reactions were carried out for 30 cycles of amplification. The annealing temperature was 60° and the extension time of 30 seconds.

Quantitation of all gels was performed by densitometry with Imagequant 5.1 software. Care was taken during photography and autoradiography to ensure that no portion of the image was saturated. Longer-exposure gel photographs are displayed in the figures to show sometimes low-abundance bands.

Primers used for the PCR are shown below in Table 3. Successful insertion would produce 327 and 258 bp EcoRI fragments; if insertion were to occur in the opposite orientation, 308 and 277 bp bands would result. More than 7% of PCR products produced the expected EcoRI fragments in a donor concentration-, overhang-, and ZFN-dependent manner (FIG. 2B, lane 3).

PCR products were also assayed for percent modification using the CEL-I Surveyor™ assay (Transgenomics). 28±5% of chromosomes were cleaved by the ZFNs in this experiment as measured by the CEL-I assay; the efficiency of donor capture was therefore as high as 27%.

TABLE 3

Oligos and Primers used for AAVS1

| Use (name) | Sequence |
|---|---|
| Insertion (AAVS1 F) | 5'-gcc agc tta ggt gag aat tcg gcg gat ccc gaa gct tgc taa ctc agc c-3' (SEQ ID NO: 68) |
| Insertion (AAVS1 R) | 5'-tgg cgg ctg agt tag caa gct tcg gga tcc gcc gaa ttc tca cct aag c-3' (SEQ ID NO: 69) |
| PCR (AAVS1 CEL-I F2) | 5'-ccc ctt acc tct cta gtc tgt gc-3' (SEQ ID NO: 70) |
| PCR (AAVS1 CEL-I R1) | 5'-ctc agg ttc tgg gag agg gta g-3' (SEQ ID NO: 71) |

The donor that could not correctly base pair with the AAVS1 overhangs was inserted into the chromosome at a markedly lower frequency (3%), (FIG. 2B, lane 6).

Example 3

NHEJ Derived Donor Capture in GS

To demonstrate that NHEJ-capture of a linear donor was neither locus nor cell-type specific, we extended this same technique to the GS gene in Chinese hamster ovary cells (CHO cells; *Cricetulus griseus*). In this experiment, donors analogous to those described above were cotransfected with ZFNs that cleave the GS gene (see, also, co-owned United States Patent Publication No. 20100129869). Oligos used for the donor construction are shown below in Table 4. In addition, as described above, identical versions lacking the first four bases, and versions with the first four bases changed to 5'-aaga-3' and 5'-tctt-3', respectively were used.

One million CHO-K1 cells, 3 µg 2A-linked GS ZFNs, and 2000, 200, 20, 2, or 0 nM of the GS donor were transfected in 100 µL. The donor was made by annealing the oligos shown below in Table 4 as described above for AAVS1. For comparison we performed SDSA-mediated targeted-integration reactions at GS by co-transfecting 20 µg of either donor plasmid with the 2A-linked ZFNs. For analysis of donor capture via NHEJ, the GS locus was PCR amplified as described above using the primers shown below in Table 4 and the product was subjected both to the to the CEL-I and the RFLP knockin assay as described above.

Figure 2C:
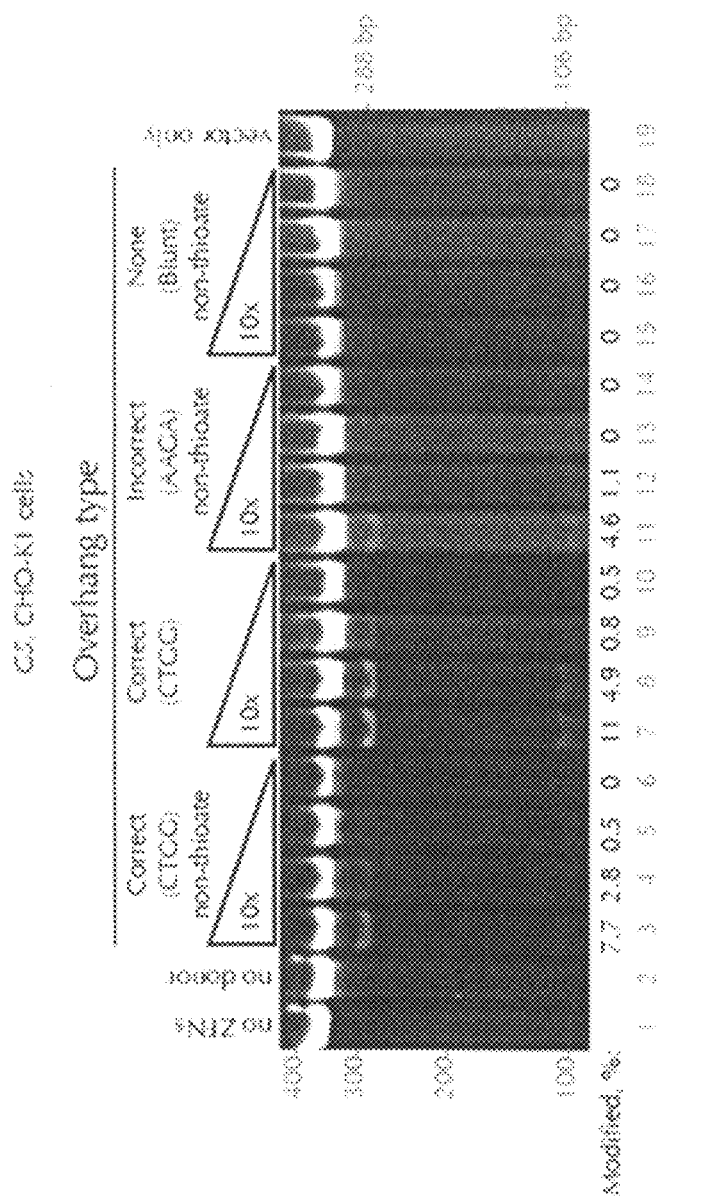
FIG. 2C shows results of PCR-based RFLP knock-in assays measuring NHEJ-based capture at the GS locus in CHO-K1 cells. Four ten-fold dilutions of donor DNAs with the indicated overhang types and phosphorothioate usage were co-transfected with the GS ZFNs.
Figure 2D:
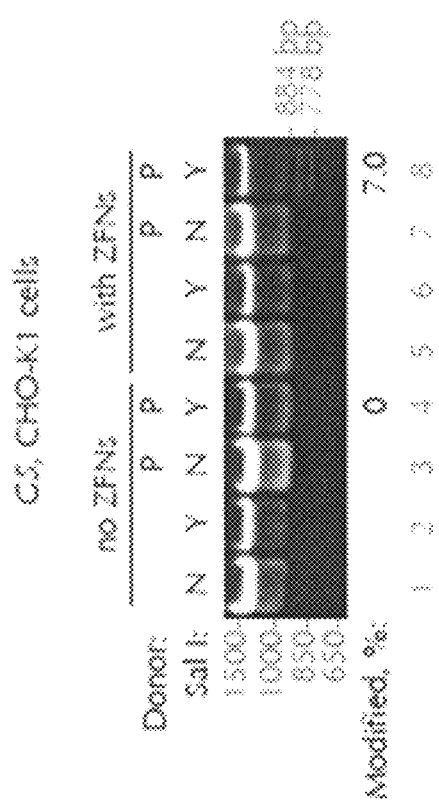
FIG. 2D shows targeted integration at GS via homology-directed repair. CHO-K1 cells were transfected with and without a plasmid donor (P) designed to insert a 17 bp patch. Correct insertion of the patch produces 884 and 778 bp fragments upon BamHI digestion (lanes 8). For FIGS. 2B-2D the percentage of modified chromosomes and lane numbers are shown below each lane in black and grey text, respectively; the position of the molecular weight markers used is shown in grey text on the left of the gel.

Eleven percent of chromosomes contained an insertion of the donor DNA (FIG. 2C, lane 7). As at least 24±3% of GS loci were ZFN-cleaved in this experiment, the efficiency of donor capture was as high as 46%. When a non-phosphorothioate donor was used, 8% of chromosomes accepted a donor insertion and insertion became more sensitive to low donor concentration (FIG. 2C, lanes 3-6). Similar to the results obtained at the AAVS1 locus, synthetic donor insertion at GS took place at lower frequency with non-complementary-overhang donors and was abolished when blunt-ended donors were used. (FIG. 2C, lanes 11-18). At the GS locus, the frequency of donor integration via NHEJ was comparable to HDR-mediated insertion of a 17 bp sequence using a conventional plasmid donor (FIG. 2C, lane 7 and FIG. 2D lane 8). As 22±3% of GS loci were ZFN-cleaved in this experiment, the integration efficiency was as high as 31%.

TABLE 5

Fidelity of donor capture by NHEJ at GS in CHO cells

|  | Normal Donor | Phosphorothioate Donor |
|---|---|---|
| Total sequence reads: | 56 | 32 |
| Perfect insertions: | 5 | 17 |
| Deletion of donor only: | 33 | 8 |
| Deletion of chromosome only: | 0 | 2 |
| Deletion of donor and chromosome: | 18 | 5 |
| Perfect, as % of total: | 9% | 55% |
| Estimate of cells with perfect insertion: | 0.7% | 6% |

The percent of cells with a perfect insertion was obtained by multiplying the frequency of RFLP-positive cells in FIG. 2C (7.7%, and 11%) by the probability of a perfect insertion (9% and 55%).

Example 4

NHEJ Driven Capture into a Deleted Region of the Genome

Transfection of two separate ZFN pairs results in the creation of two DSBs and occasionally, loss of the intervening DNA to create a deletion (Lee et al (2010) *Genome Res.* 20(1):81-9). As overhangs created by different ZFN pairs will have non-complementary ends, deletion formation requires microhomology-mediated end joining (MMEJ). To see if donors could be captured at the site of deletions, we created donors compatible with the outer two overhangs generated by

TABLE 4

Oligos and Primers used for GS

| Use (name) | Sequence |
|---|---|
| Insertion F | 5'-ctg ggc tta ggt gag aat tcg gcg gat ccc gaa gct tgc taa ctc agc c-3' (SEQ ID NO: 72) |
| Insertion R | 5'-cca ggg ctg agt tag caa gct tcg gga tcc gcc gaa ttc tca cct aag c-3' (SEQ ID NO: 73) |
| PCR GS F5928 | 5'-ggg tgg ccc gtt tca tct-3' (SEQ ID NO: 74) |
| PCR GS R6272 | 5'-cgt gac aac ttt ccc ata tca ca-3' (SEQ ID NO: 75) |

To confirm the results of our PCR-based donor insertion assay, we isolated CHO cell clones bearing insertions of donor sequence. 135 clones were screened by BamHI digestion to find 11 clones (8%) with bona fide donor insertion as confirmed by DNA sequencing.

Figure 3A:
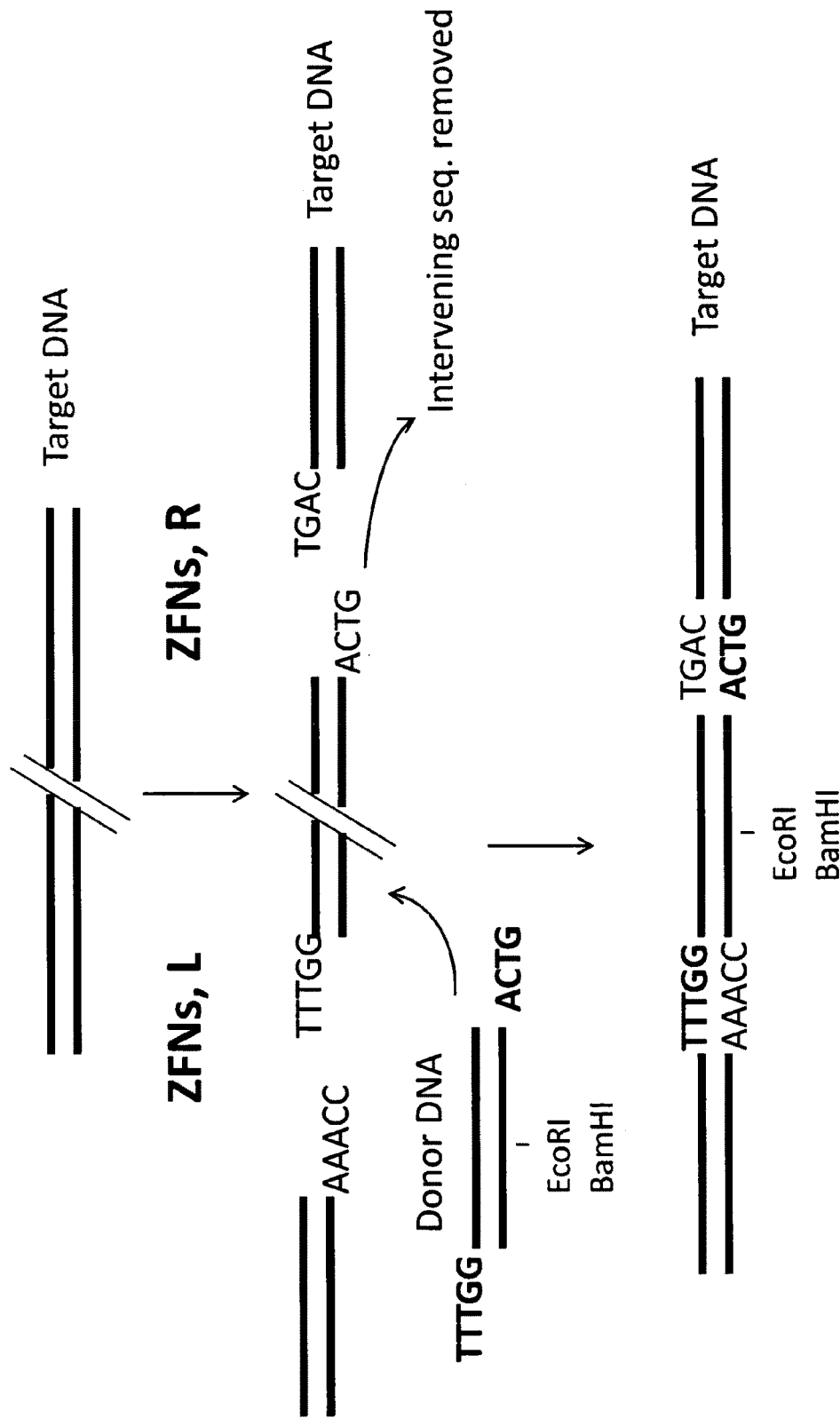
FIG. 3A is a schematic depicting dual ZFN cleavage at POU5F1 resulting in 5 bp 5' overhangs from the left ZFN pair and 4 bp 5' overhangs from the right ZFN pair followed by in vivo ligation of a complimentary-overhang donor. The donor contains both BamHI and EcoRI restriction enzyme sites.

Insertion of donors with incorrectly base-paired ends requires the inexact joining mode of NHEJ. The lower-but-appreciable frequency of inexact end joining suggested that some donors might not have been faithfully inserted even when perfectly complementary overhangs were provided. To determine the fidelity of donor insertion, a pool of donor-dependent PCR products was cloned and sequenced. Fifty-five percent of insertions contained perfectly ligated junctions when phosphorothioate donors were used; this frequency dropped to only 9% with use of standard DNA donors (Table 5). Exonuclease digestion of the donor and chromosomal ends at the break resulted in imperfect insertion in the remainder of events.

two ZFN pairs targeted to the POU5F1 locus in K562 cells and three ZFN pairs at the BAK locus in CHO-K1 cells (diagramed in FIG. 3A). BAK deletions A and B share the right-hand ZFN pair and have similar left-hand ZFN pairs, offset by 3 bp. For the BAK insertions, the first 5 bp of the lox P F oligo used for POU5F1 was replaced by 5'-cagc-3' (deletion A) or 5'-tggc-3' (deletion B) in combination with the lox P R oligo used for POU5F1 with its first 4 bp changed to 5'-ccca-3'. Table 6 shows the oligos used to the donor insertion and for PCR, where the loxP site is underlined on the donor oligos.

ZFN pairs were transfected individually and in combination with the second pair, both with and without inclusion of a donor oligonucleotide. One million K562 cells, 2 µg each POU5F1 ZFN, and 40, 4, or 0 µM donor were transfected in 100 µL. Deletion formation was assayed by PCR amplification as described above of the POU5F1 and BAK loci. Sequences of oligonucleotides used for insertion and PCR are shown below in Table 6. All oligonucleotides were 5' phosphorylated and contain phosphorothioate linkages between the 5' terminal two bases unless otherwise noted.

TABLE 6

Oligos and Primers used for POU5F1 and BAK

| Use (name) | Sequence |
|---|---|
| Insertion IoxP F-POU5F1 | 5'-ttt ggg aat tc <u>a taa ctt cgt ata gca tac att ata cga agt tat</u> gga tcc-3' (SEQ ID NO: 76) |
| Insertion IoxP R-POU5F1 | 5'-tgc agg atc <u>cat aac ttc gta taa tgt atg cta tac gaa gtt at</u> g aat tc-3' (SEQ ID NO: 77) |
| PCR Group 3F-POU5F1 | 5'-gat aga acg aga ttc cgt ctt ggt gg-3' (SEQ ID NO: 78) |
| PCR Group 4R-POU5F1 | 5'-gca gag ctt tga tgt cct ggg act-3' (SEQ ID NO: 79) |
| PCR GJC 24F-BAK | 5'-cat ctc aca tct gga cca cag ccg-3' (SEQ ID NO: 80) |
| PCR GJC 163R-BAK | 5'-ctg cgg gca aat aga tca c-3' (SEQ ID NO: 81) |

Figure 3B:
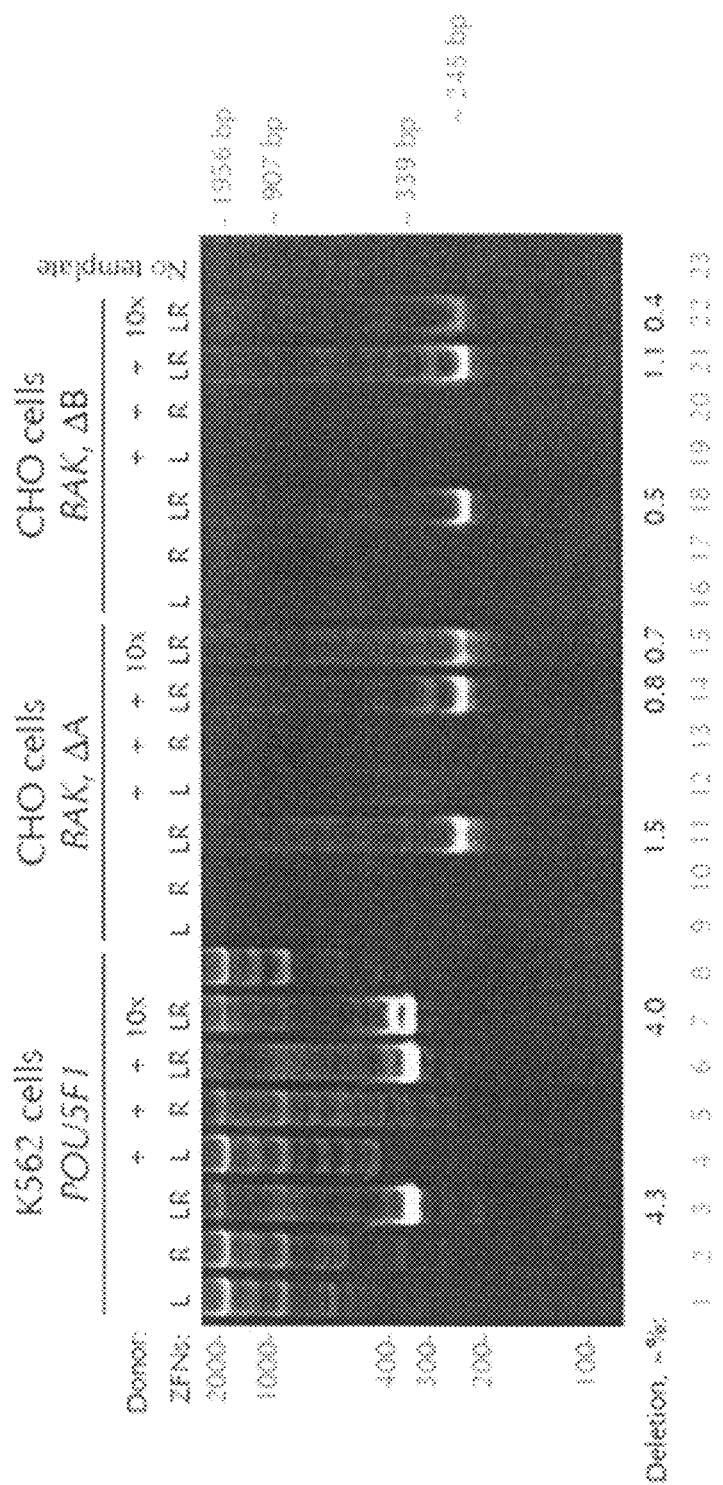
FIG. 3B depicts NHEJ capture at a POU5F1 deletion in K562 cells and at BAK in CHO-K1, cells as detected by PCR. Left (L) and right (R) ZFN pairs were transfected individually and in combination (LR), with (+) and without (−) donor cotransfection. The sizes of significant PCR products are shown on the right side of the gel, POU5F1 in the left column, BAK in the right. Capture of donor sequences will result in a doublet in the PCR (see for example lanes 7, 14 and 21 in FIG. 3B). As deletions are heterogeneous, their expected sizes are indicated with tildes. Due to the relatively small deletion made in POU5F1, amplification of the wild-type locus is seen (1956 bp), as well as a ~907 bp PCR-mediated deletion product likely formed by annealing of two Alu elements in intron 2 of POU5F1. The deletion quantitation shown below the gel is from an independent analysis of cell pools described in the main text.

Only when both ZFN pairs were co-transfected did deletion-specific PCR products appear (FIG. 3B, lanes 3, 11, and 18, e.g.). For POU5F1, deletion of ~1617 bp resulted in formation of a ~339 bp deletion-specific band (lane 3). For BAK, deletion of ~5833 or 5836 bp resulted in formation of ~245 or 242 bp deletion-specific bands (deletions A and B, respectively, lanes 11 and 18). When the donor was co-transfected with both ZFN pairs, a new band appeared with a size corresponding to donor insertion at the deletion (FIG. 3B, lanes 6 and 7, 51 bp larger; lanes 14, 15, 21, and 22, 50 bp larger). The efficiency of insertion into POU5F1 increased proportionally when the donor concentration was raised tenfold to 50 µM; in contrast, insertion into BAK was reduced when the donor concentration was increased to 50 µM (compare lane 6 with lane 7 and lanes 14 and 21 with lanes 15 and 22).

The donor used in these experiments contains both BamHI and EcoRI restriction enzyme sites. When the deletion PCR products from FIG. 3B were incubated with either BamHI or EcoRI, the donor-dependent bands were digested. For both POU5F1 and BAK, the sizes of the digestion products exactly matched the sizes expected from donor insertion. Donor insertion into POU5F1 produced 230 and 160 bp BamHI products and 270 and 120 bp EcoRI products (FIG. 3C, lanes 5 and 8, 6 and 9); insertion into BAK deletion A gave 176 and 119 bp BamHI products and 216 and 79 bp EcoRI products (lanes 14 and 17, 15 and 18). For BAK deletion B, the sizes of the smallest digestion products are 3 bp less. Quantitation of the digests indicated that 52% of POU5F1 deletions and 10-20% of BAK deletions acquired a donor insertion.

Asymmetry of the BamHI and EcoRI sites within the donor allows digestion to report the orientation specificity of donor insertion. Insertion in the reverse orientation will yield an approximate reversal of the digestion products (similar to FIG. 2B lane 6). A detectable but very minor fraction of POU5F1 and BAK deletion A insertions are in the incorrect orientation (seen most clearly in FIG. 3C lanes 9 and 15); for BAK deletion B, no bands consistent with inverted insertion are visible (lane 24).

Figure 3C:
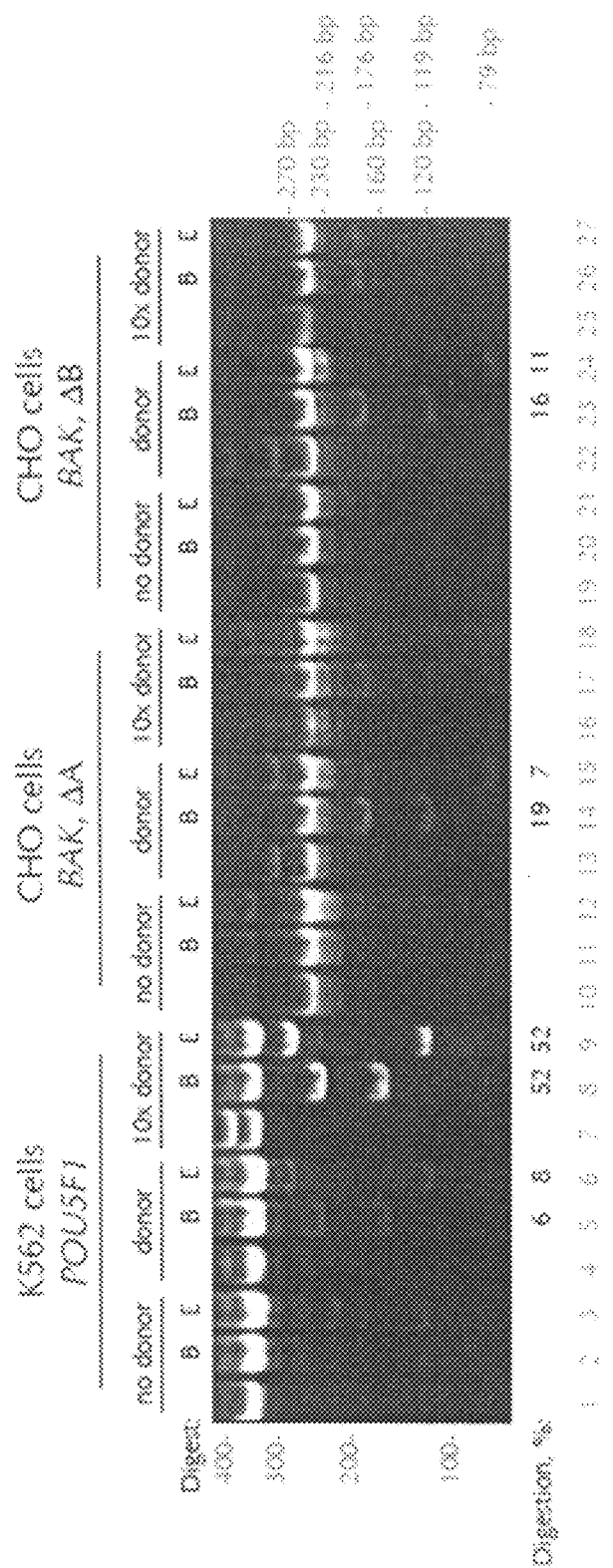
FIG. 3C depicts a restriction enzyme digestion that confirms targeted integration of the donor molecule containing the restriction sites into the POU5F1 and BAK deletions. PCR reactions from lanes 3, 6, 7, 11, 14, 15, 18, 21, and 22 in FIG. 3B were divided into thirds, one third was left uncut (blank), one third was digested with BamHI (B), and one third was digested with EcoRI (E). The sizes of BamHI and EcoRI digestion products are shown on the right side of the gel, POU5F1 in the left column, BAK in the right. The amount of digested DNA was determined by densitometry.

To confirm these results and to determine the deletion and deletion plus insertion frequency, cells from all lanes in FIG. 3C containing a deletion-specific PCR product were diluted, grown for 2 weeks, and 96 or more ten-cell pools (>960 cells) assayed by PCR as above. Approximately 4% of K562 cells treated with POU5F1 ZFNs and 1% of CHO-K1 cells treated with BAK ZFNs contained either a deletion or a deletion and a donor insertion. The deletion frequency did not increase when donor was present. These data are shown under their respective lanes in FIG. 3B.

The overall fidelity of donor insertion at deletions was determined by cloning and sequencing donor insertion events. Similar to the 55% perfect insertion frequency found at GS, 42% of POU5F1 donors and 69% of BAK deletion A donors were faithfully inserted (Table 7 below). A major failure mode for correct insertion into BAK deletion A resulted in disruption of the EcoRI site. Consistent with this, EcoRI treatment did not completely digest the donor-dependent band for BAK deletion A (FIG. 3C lane 15).

TABLE 7

Fidelity of donor capture at deletions by NHEJ

|  | POU5F1 | BAK, ΔA |
|---|---|---|
| Total sequence reads: | 33 | 32 |
| Perfect insertions: | 14 | 22 |
| Deletion of donor only: | 6 | 4 |
| Deletion of chromosome only: | 4 | 2 |
| Deletion of donor and chromosome: | 9 | 4 |
| Perfect, as % of total: | 42% | 69% |
| Estimate of cells with perfect insertion: | ~0.8% | ~0.1% |

The percent of cells with a perfect insertion was obtained by multiplying the approximate frequency of RFLP-positive cells in FIG. 3B (~2%, and ~0.2%) by the probability of a perfect insertion (42% and 69%).

Example 5

Non-Specific Integration

DNA can also integrate into double-strand breaks via non-homology-dependent mechanisms. DSBs are spontaneously generated in the cell due to errors in DNA metabolism and can also created by inappropriate ZFN action.

Figure 4:
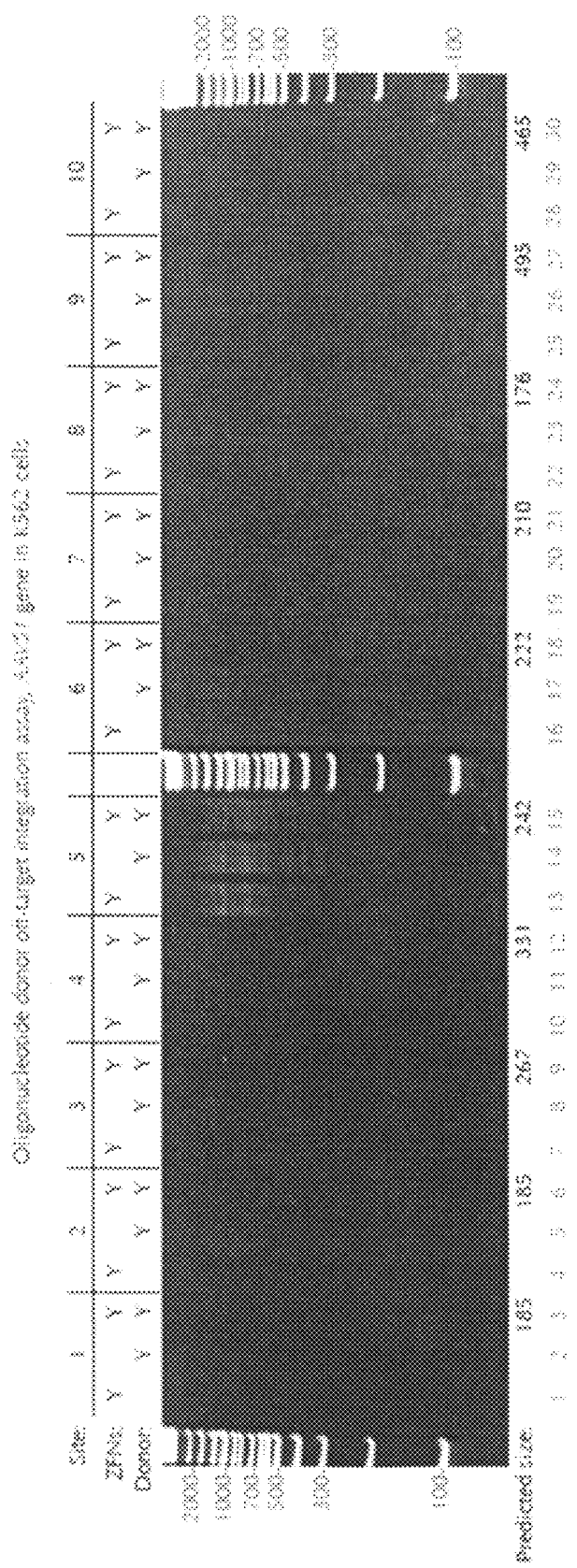
FIG. 4 shows analysis of off-target ZFN action. Samples were treated with ZFNs only, donor only, and ZFNs plus donor and then were assayed for off-target oligonucleotide integration at the top ten potential AAVS1 off-target sites by PCR specific for the junction of the oligonucleotide and each off-target locus. The size of the PCR product expected from the off-target integration is shown below each lane.

Accordingly, we searched for off-target integration events at AAVS1 by inspection of the 10 most-likely off-target sites predicted ab initio from the known specificity of the AAVS1 ZFNs (Hockemeyer et al (2009) *Nat Biotechnol* 27 p. 851-857). A PCR primer specific to each of the ten loci was paired with a PCR primer in the oligonucleotide donor. Pools of cells treated with ZFNs and donor molecules were assayed for the junction between the donor and each off-target site. As shown in FIG. 4, no such junctions were observed.

Example 6

TALEN Mediated Capture of Oligonucleotide Duplex by NHEJ

The methods of the invention were also used with TALE-nucleases to drive capture of partially single stranded oligonucleotide duplexes. TALENs were made to cleave the NTF3 target locus as described in Miller et al (2011) *Nat. Biotechnol.* February; 29(2):143-8. Epub 2010 Dec. 22. Briefly, nucleic acid vectors encoding a pair of TALENs was made as described in Miller et al, NT-L+28 and NT-R+63 and expressed in K562 cells in the presence of the oligonucleotide duplex donor comprising 4 base pair single strand overhangs (FIG. 5A). Binding sites for the TALENs on the NTF3 target are shown in FIG. 5B. Junctions between successfully integrated duplex and genomic DNA were then amplified using one primer that anneals within the duplex and one primer that anneals to the native NTF3 locus.

The resulting amplicons were cloned and sequenced. The "expected" sequence depicted in FIG. 5C at top indicates the sequence that would result from a perfect ligation of oligonucleotide duplex to the cleaved locus. The box highlights the location of the duplex overhang in the junction sequences. The bottom two lines of FIG. 5C (SEQ ID NOs:103 and 104) show junction sequences obtained from this study. As shown, eleven junction sequences resulted from perfect ligation of duplex to the cleavage overhang, while one junction sequence exhibited a short deletion (12 bp) consistent with resection prior to repair by NHEJ.

Next, the oligonucleotide duplex from panel B was used, which has a 4 bp overhang that is shifted by one base relative to the duplex shown in panel A. As shown in the bottom four lines of FIG. 5D (SEQ ID NOs:106 to 109), four distinct junction sequences were identified, which each exhibit short deletions consistent with resection prior to NHEJ-mediated repair.

Together, the data show that the non-homologous end joining machinery in mammalian cells is generally capable of capturing exogenous linear donor DNA at targeted double-strand breaks and that this reaction is strongly promoted by the presence of complementary single-strand donor overhangs.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of non-homologous end joining (NHEJ)-mediated targeted integration of a linear nucleic acid molecule into the genome of a mammalian cell, the method comprising:

introducing a linear nucleic acid molecule into the mammalian cell, the linear nucleic acid molecule comprising a double-stranded sequence of interest having first and second ends and first and second single-stranded nucleotides between 1 and 10 nucleotides in length at the first and second ends of the double-stranded sequence; and creating a double-stranded break using a nuclease in an endogenous locus of the genome of the mammalian cell such that the linear nucleic acid molecule is integrated at the site of the double-stranded break and further wherein the nuclease comprises a TALE domain and the first and second single-stranded nucleotides are 100% complementary to the overhangs of the double-stranded break in the mammalian genome created by the nuclease; and annealing the first and second single-stranded nucleotides of the donor to the overhangs of the double-stranded break in the mammalian genome, thereby directly integrating the donor at the site of double-stranded break by NHEJ-mediated targeted integration.

2. The method of claim 1, wherein the linear nucleic acid molecule further comprises one or more phosphorothioate phosphodiester bonds between one or more nucleic acids.

3. The method of claim 1, wherein one or more nucleic acids are methylated or comprise non-natural nucleotide analogs.

4. The method of claim 1, wherein the sequence of interest comprises a polynucleotide encoding a functional polypeptide.

5. The method of claim 4, wherein the polypeptide is selected from the group consisting of an antibody, an antigen, an enzyme, a growth factor, a receptor, a hormone, a lymphokine, a cytokine, a reporter and combinations therefore.

6. The method of claim 1, wherein the sequence of interest comprises a sequence encoding a functional RNA.

7. The method of claim 1, wherein the sequence of interest comprises an integration site.

* * * * *